(12) United States Patent
Ku et al.

(10) Patent No.: US 11,129,861 B2
(45) Date of Patent: Sep. 28, 2021

(54) METHODS FOR TREATING INFLAMMATORY DISEASES

(71) Applicant: OKCHUNDANG CO., LTD., Daegu (KR)

(72) Inventors: Seong Min Ku, Busan (KR); Tae Hun Ku, Busan (KR); Chul Jong Jung, Ulsan (KR); Jeong Gyun Seo, Daegu (KR); Hye Ran Gong, Daegu (KR); Sae Kwang Ku, Daegu (KR); Seok Man Park, Daegu (KR); Ryong Kong, Jeollabuk-do (KR); Xian Li, Daegu (KR); Gyung Yun Beik, Daegu (KR); Yoeng Eun Yu, Daegu (KR); Hee Jeong Ryu, Daegu (KR); Gyu Hyeon Kim, Daegu (KR)

(73) Assignee: OKCHUNDANG CO., LTD., Daegu (KR)

( * ) Notice: Subject to any disclaimer, the term of this patent is extended or adjusted under 35 U.S.C. 154(b) by 595 days.

(21) Appl. No.: 15/885,122

(22) Filed: Jan. 31, 2018

(65) Prior Publication Data
US 2018/0214499 A1    Aug. 2, 2018

(30) Foreign Application Priority Data

Feb. 1, 2017 (KR) .................. 10-2017-0014447
Jan. 30, 2018 (KR) .................. 10-2018-0011492

(51) Int. Cl.
| | |
|---|---|
| A61K 36/258 | (2006.01) |
| A61K 36/342 | (2006.01) |
| A61P 13/12 | (2006.01) |
| A61K 36/07 | (2006.01) |
| A61K 36/64 | (2006.01) |
| A61K 31/70 | (2006.01) |
| A61P 17/00 | (2006.01) |
| A61P 37/08 | (2006.01) |
| A61P 7/00 | (2006.01) |
| A61P 11/06 | (2006.01) |
| A61P 27/02 | (2006.01) |
| A61P 1/02 | (2006.01) |
| A61P 27/16 | (2006.01) |
| A61P 1/00 | (2006.01) |
| A61P 11/00 | (2006.01) |
| A61P 1/04 | (2006.01) |
| A61P 15/02 | (2006.01) |
| A61P 19/06 | (2006.01) |
| A61P 19/02 | (2006.01) |
| A61P 29/00 | (2006.01) |
| A61P 1/16 | (2006.01) |
| A61P 13/10 | (2006.01) |

(52) U.S. Cl.
CPC ............ *A61K 36/342* (2013.01); *A61K 31/70* (2013.01); *A61K 36/07* (2013.01); *A61K 36/258* (2013.01); *A61K 36/64* (2013.01); *A61P 1/00* (2018.01); *A61P 1/02* (2018.01); *A61P 1/04* (2018.01); *A61P 1/16* (2018.01); *A61P 7/00* (2018.01); *A61P 11/00* (2018.01); *A61P 11/06* (2018.01); *A61P 13/10* (2018.01); *A61P 13/12* (2018.01); *A61P 15/02* (2018.01); *A61P 17/00* (2018.01); *A61P 19/02* (2018.01); *A61P 19/06* (2018.01); *A61P 27/02* (2018.01); *A61P 27/16* (2018.01); *A61P 29/00* (2018.01); *A61P 37/08* (2018.01)

(58) Field of Classification Search
None
See application file for complete search history.

(56) References Cited

U.S. PATENT DOCUMENTS

2019/0358283 A1*  11/2019  Ku ................ A61K 36/342

FOREIGN PATENT DOCUMENTS

| CN | 101990964 | * | 3/2011 | |
|---|---|---|---|---|
| CN | 104547496 | * | 4/2015 | |
| CN | 105661205 | * | 6/2016 | |
| KR | 10-2010-0055030 | | 5/2010 | ............ A61K 36/75 |
| KR | 2015 105561 | * | 9/2015 | |
| KR | 10-2016-0045368 | | 4/2016 | ............ A61K 36/35 |

OTHER PUBLICATIONS

Im LR et al. Inhibitory effect of Kyungohkgo in the Development of 2,4-Dinitrochlorobenzene-induced atopic dermatitis in NC/Nga mice. *Arch Pharm Res.* 2011;34(2):317-321.

Yoon YP et al. Effects of lupenone, lupeol, and taraxerol derived from *Adenophora triphylla* on the gene expression and production of airway MUC5AC Mucin. *Tuberc Respir Dis.* 2015;78:210-7.

Chun J et al. A triterpenoid saponin from *Adenophora triphylla* var. japonica suppresses the growth of human gastric cancer cells via regulation of apoptosis and autophagy. *Tumour Biol.* 2014; 35:12021-30.

Jung HL et al. Effects of *Panax ginseng* supplementation on muscle damage and inflammation after uphill treadmill running in humans. *Am J Chin Med.* 2011;39(3):441-50.

(Continued)

*Primary Examiner* — Ralph J Gitomer
(74) *Attorney, Agent, or Firm* — Harness, Dickey & Pierce, P.L.C.

(57) ABSTRACT

The present invention provides a composition containing, as active ingredients, *Panax ginseng*, *Adenophora triphylla*, *Wolfiporia extensa*, *Rehmannia glutinosa*, and Mel for an antitussive, expectorant, or anti-inflammatory action, and a composition for preventing, alleviating, or treating a respiratory disease. The present invention provides a compositions having excellent effects compared with an existing antitussive agent and expectorant agent. The compositions of the present invention are a naturally derived material and has little cytotoxicity, and thus is expected to be safely used as a medicine or food composition having antitussive, expectorant, and anti-inflammatory effects.

2 Claims, 17 Drawing Sheets

(56) References Cited

OTHER PUBLICATIONS

Shergis JL et al. Therapeutic potential of *Panax ginseng* and ginsenosides in the treatment of chronic obstructive pulmonary disease. *Complement Ther Med.* 2014;22(5):944-53.

Jeong JW et al. Ethanol extract of *Poria cocos* reduces the production of inflammatory mediators by suppressing the NF-kappaB signaling pathway in lipopolysaccharide-stimulated RAW 264.7 macrophages. *BMC Complement Altern Med.* 2014;14(1):101-8.

Baek GH et al. *Rehmannia glutinosa* suppresses inflammatory responses elicited by advanced glycation end products. *Inflammation* 2012;35(4):1232-41.

Manjunath DH and Lee SC. The anti-inflammatory and wound healing properties of honey. *Eur Food Res Technol.* 2014;239:1003-14.

Office Action from corresponding Korean Patent Application No. 10-2018-0011492, dated Jan. 2, 2019.

Lee, Jeong-hyeok et al., "A study of modern application of Kyungohkgo through historical analysis of its virtues", Journal of Institute of Oriental Medicine of DaeJeon University, pp. 25-34, 2016.

Kang, K. W., "Study on the anti-inflammatory effect and the isolation of new constituents from the roots of Adenophora triphyl", Master's Thesis of Dongguk University graduate school, 2011.

\* cited by examiner

METHODS FOR TREATING INFLAMMATORY DISEASES

CROSS REFERENCE TO RELATED APPLICATIONS

This application claims priority to Korean Patent Application Nos. 10-2017-0014447, filed on Feb. 1, 2017 and 10-2018-0011492, filed on Jan. 30, 2018, with the Korean Intellectual Property Office, the disclosures of which is incorporated herein in its entirety by reference.

FIELD

The present invention relates to compositions for antitussive, expectorant or anti-inflammation

BACKGROUND

Cough is defined as a forced expulsive maneuver, usually against a closed glottis which is associated with a characteristic sound. Cough can be the result of several respiratory tract disorders which may require drug treatment for its relief. Chronic cough is disturbing to the patient as it monumentally affects the patient's quality of life. Broncho-constriction is significant in cough induction since the process stimulates intrapulmonary rapidly adapting receptor, a type of cough receptor to cause or enhance the sensitivity of the cough. Rapidly adapting receptor activation initiates bronchospasm and mucus secretion via parasympathetic reflexes.

Coughing is one of common symptoms associated with many respiratory diseases such as asthma, chronic bronchitis and pneumonia. Cough with copious phlegm is a common symptom of respiratory diseases. Increased sputum may cause irritation of the respiratory mucosa, which leads to coughs. The blocks of bronchioles will not only cause asthma, but also cause secondary infection which results in further damage of the respiratory tract leading to the increased cough, sputum and asthma. In some cases, excessive phlegm may cause respiratory depression or suffocation. In addition, inflammatory processes also have been involved in the pathogenesis of various respiratory disorders. It, therefore, has been believed that drugs have simultaneous antitussive, expectorant and anti-inflammatory activities will be showed reliable and favorable protective effects against various respiratory disorders, especially originated from toxic environment.

Cough can be described as non-productive (dry) or productive (chesty). Antitussives are effective in managing non-productive cough but not as effective with productive cough except when the antitussive has expectorant property. In addition, inflammatory processes also have been involved in the pathogenesis of various respiratory disorders. It, therefore, has been believed that drugs have simultaneous antitussive, expectorant and anti-inflammatory activities will be showed reliable and favorable protective effects against various respiratory disorders, especially originated from toxic environment. Recently, many pharmacological agents have been shown to have both antitussive and expectorant effect making them useful for both chesty and dry cough. The essence of such dual effect is affirmed by the fact that many pharmaceutical formulations have such combination. Presently cough can be regulated by usual drugs such as antitussive and expectorant drugs, like codeine, theobromine (TB) and ambroxol (AM) but real treatment concerns the pathology that induces cough. The problem is not to only use an efficient therapy against coughing, which will inevitably bring side effects. TB, formerly known as xantheose, is a bitter alkaloid of the cacao plant, and has an antitussive effect superior to codeine by suppressing vagus nerve activity, but TB poisoning may be occurred result from the chronic or acute consumption of large quantities, especially in the elderly. AM is a secretolytic agent used in the treatment of respiratory diseases associated with viscid or excessive mucus. However, caution is suggested for patients with gastric ulceration, and usage of AM during the first trimester of pregnancy is not recommended. Adrenocorticosteroids, including dexamethasone (DEXA) have been used for treatment of various allergic and inflammatory diseases, and they showed favorable ameliorating effects, but they also have been showed serious side effects including fetal immunodeficiency. Therefore, there is an increasing demand for searching the antitussive, expectorant and anti-inflammatory medicine in the therapy of various respiratory disorders and its pathology.

The present inventors, during continuous research to develop a naturally derived medicine solving the above problems and having antitussive and expectorant effects and an anti-inflammatory effect without side effects, found facts that a composition containing *Adenophora triphylla, Panax ginseng, Wolfiporia extensa, Rehmannia glutinosa*, and mel mixed with each other showed a similar or superior antitussive effect compared with theobromine as an existing antitussive agent, showed a similar or superior expectorant effect compared with ambroxol as an existing expectorant agent, and showed a similar anti-inflammatory effect to dexamethasone as an existing anti-inflammatory agent, and thus the present inventors completed the present invention.

PATENT DOCUMENTS (Patent Document 01) Korean Patent Publication No. 10-2010-0055030
(Patent Document 02) Korean Patent Publication No. 10-2016-0045368

SUMMARY

Technical Problem

The present inventors endeavored to develop a naturally derived medicine having an anti-inflammatory effect while having antitussive and expectorant effects without side effects. As a result, the present inventors established that a composition containing *Adenophora triphylla, Panax ginseng, Wolfiporia extensa, Rehmannia glutinosa*, and mel mixed with each other showed excellent antitussive and expectorant effects compared with theobromine and ambroxol as well as a similar anti-inflammatory effect to dexamethasone, and thus completed the present invention.

Therefore, an aspect of the present invention is to provide a pharmaceutical composition for an antitussive, expectorant, or anti-inflammatory action.

Another aspect of the present invention is to provide a food composition for an antitussive, expectorant, or an anti-inflammatory action.

Still another aspect of the present invention is to provide a pharmaceutical composition for preventing or treating a respiratory disease.

Another aspect of the present invention is to provide a food composition for preventing or alleviating a respiratory disease.

Still another aspect of the present invention is to provide a method for treating cough, sputum, or an inflammatory disease.

Another aspect of the present invention is to provide a method for treating a respiratory disease.

Technical Solution

In accordance with an aspect of the present invention, there is provided a pharmaceutical composition for an antitussive, expectorant, or anti-inflammatory action, the composition contains, as active ingredients, *Adenophora triphylla*, *Panax ginseng*, *Wolfiporia extensa*, *Rehmannia glutinosa*, and mel.

The present inventors endeavored to develop a naturally derived medicine having an anti-inflammatory effect while having antitussive and expectorant effects without side effects. As a result, the present inventors established that a composition containing *Adenophora triphylla*, *Panax ginseng*, *Wolfiporia extensa*, *Rehmannia glutinosa*, and mel mixed with each other showed excellent antitussive and expectorant effects compared with theobromine and ambroxol as well as a similar anti-inflammatory effect to dexamethasone.

*Panax ginseng* is a perennial plant of the family Araliaceae and is 30-60 cm tall. Stem straighten each year, and one flower stalk at apex continues, and three to six petioles are verticillate. Leaves have long petioles, are divided into three to five lead blades, and are palmately compound. Hairs are present on veins on the upper surface of leaf. In summer, one thin flower stalk comes out, and 4-40 pale yellow-green small flowers are hung at the terminal. There are five petals and stamens and one pistil, and an ovary is disposed inferior. The fruit is a drupe, compressed-globose, and bright red when ripened. Herein, *Panax ginseng* means roots thereof.

*Adenophora triphylla* is a perennial herb of the family Campanulaceae. Stems are straight and 50-100 cm in height. White sap comes out when stems are broken. Leaves are long oval and five to four leaves are verticillate. Both stems and leaves have hairs. From July to October, several purplish flowers are verticillate. The corolla is bell-shaped and 13-22 mm long. The style is divided into three, and is somewhat longer than corolla. The flower has five stamens, which are separated from peduncle and the staminode has a broad bottom portion and hairs.

*Wolfiporia extensa* is a basidiomycete of the family of Polyporaceae. The *sclerotium* is formed in the pine root 10-30 cm underground and has an irregular shape. It has a blackish reddish-brown, wrinkled surface and a white or red inside portion.

*Rehmannia glutinosa* is a perennial plant of the family Orobanchaceae and is about 30 cm in height. Leaves are elliptical, come out from the roots, and produces pink-purple flowers that bloom in June and July. Herein, *Rehmannia glutinosa* means roots thereof.

Mel refers to the sugar that are sucked and collected from the flower nectary by honey bees or *Apis mellifera*.

As used herein, the term "antitussive" refers to the action to suppress or alleviate cough. Cough diseases are classified into mucus non-secreting (dryness) or mucus secreting (pectoriloquy and wet recurrent). It has been known that existing antitussive agents are very effective on dry cough but are not effective on wet recurrent cough unless accompanied by an expectorant action.

As used herein, the term "expectorant" refers to the action to promote the mucus secretion of the body to resolve the collected sputum.

As used herein, the term "inflammation" refers to a normal and protective in vivo defense mechanism that occurs locally against to the tissue damage caused by irritants of in vivo metabolites due to physical injuries, harmful chemicals, and microbial infections. As used herein, the term "anti-inflammation" refers to the suppression, alleviation, or removal of the inflammation.

The pharmaceutical composition for an anti-inflammatory action of the present invention is a pharmaceutical composition for preventing or treating an inflammatory disease.

According to an embodiment of the present invention, the inflammatory disease includes dermatitis, allergy, edema, atopic disease, asthma, conjunctivitis, periodontitis, rhinitis, otitis media, laryngopharyngitis, tonsillitis, pneumonia, stomach ulcer, gastritis, Crohn's disease, colitis, hemorrhoids, vaginitis, gout, ankylosing spondylitis, rheumatic fever, lupus, fibromyalgia, psoriatic arthritis, osteoarthritis, rheumatoid arthritis, shoulder periitis, tendinitis, tendovaginitis, peritendinitis, myositis, hepatitis, cystitis, nephritis, Sjogren's syndrome, multiple sclerosis, and acute or chronic inflammatory disease.

The pharmaceutical composition for an antitussive, expectorant, or anti-inflammatory action of the present invention contains, as active ingredients, *Panax ginseng*, *Adenophora triphylla*, *Wolfiporia extensa*, *Rehmannia glutinosa*, and mel.

According to an embodiment of the present invention, the composition is prepared by mixing 4-5 wt % of *Panax ginseng*, 4-5 wt % of *Adenophora triphylla*, 8-10 wt % of *Wolfiporia extensa*, 43-48 wt % of *Rehmannia glutinosa*, and 35-40 wt % of mel.

The *Panax ginseng*, *Adenophora triphylla*, *Wolfiporia extensa*, and *Rehmannia glutinosa* contained in the composition of the present invention may be pulverized bodies, a suspension of pulverized bodies, a juice, or an extract.

The pulverized bodies may be prepared by various procedures. For example, the *Panax ginseng*, *Adenophora triphylla*, *Wolfiporia extensa*, or *Rehmannia glutinosa* is subjected to a processing procedure, such as vacuum distillation, freeze-drying, or spray drying, and then may be used as pulverized bodies in various states, such as a powdered state, a homogenized state, a sliced state, and a mashed state.

According to an embodiment of the present invention, the *Panax ginseng*, *Adenophora triphylla*, and *Wolfiporia extensa* are in a powdered state or a homogenized state, after freeze-drying.

The dispersion of pulverized bodies may be prepared by various solutions. For example, distilled water or buffer (e.g., Tris buffer or HEPES buffer) may be used.

The juice may be prepared by various procedures. For example, the juice may be prepared by using gear type juicing using a compression effect, press type juicing, crush type juicing, or enzymatic degradation type juicing.

According to an embodiment of the present invention, the *Rehmannia glutinosa* is in a juice state.

According to another embodiment of the present invention, the *Rehmannia glutinosa* is a juice having a sugar content of 10-20 brix and a solid content of 10-20%.

The extract may be prepared by various procedures. For example, the extract may be prepared by performing cold extraction, hot-water extraction, ultrasonic extraction, or reflux cooling extraction on a solvent crude extract obtained from the extraction with at least one solvent selected from the group consisting of water and $C_{1-4}$ alcohols.

The composition of the present invention may be prepared by aging a mixture of *Panax ginseng, Adenophora triphylla, Wolfiporia extensa, Rehmannia glutinosa*, and mel.

According to an embodiment of the present invention, the aging may be carried out at a temperature of 80-100° C. for 10-100 hours.

The temperature may be 84-100° C., 88-100° C., 92-100° C., 94-100° C., 80-99° C., 80-98° C., 80-97° C., 84-99° C., 88-98° C., 92-97° C., or 94-97° C. The time may be 10-90 hours, 20-90 hours, 30-90 hours, 40-90 hours, 50-90 hours, 60-90 hours, 10-80 hours, 20-80 hours, 30-80 hours, 40-80 hours, 50-80 hours, 60-80 hours or 65-75 hours.

According to another embodiment of the present invention, the aging may be carried out once or more. The aging may be carried out twice or more by further including a step of performing cooling before the second aging.

The cooling may be carried out at a temperature of 0-30° C. for 10-100 hours.

The pharmaceutical composition of the present invention may be used as a pharmaceutical composition containing a pharmaceutically effective amount of a mixture of *Panax ginseng, Adenophora triphylla, Wolfiporia extensa, Rehmannia glutinosa*, and mel and/or a pharmaceutically acceptable carrier.

As used herein, the term "pharmaceutically effective amount" refers to the amount sufficient to attain the efficacy or activity of the mixture.

The pharmaceutically acceptable carrier contained in the pharmaceutical composition of the present invention is conventionally used at the time of formulating, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain a lubricant, a humectant, a sweetener, a flavoring agent, an emulsifier, a suspending agent, and a preservative.

The pharmaceutical composition of the present invention may be administered orally or parenterally, and for example, intravenous administration, subcutaneous administration, intramuscular administration, intraperitoneal administration, topical administration, intranasal administration, intrapulmonary administration, rectal administration, intrathecal administration, ocular administration, skin administration, and transdermal administration may be employed.

An adequate dose of the pharmaceutical composition of the present invention varies depending on factors, such as the formulating method, manner of administration, patient's age, body weight, or gender, severity of disease, food, time of administration, route of administration, excretion rate, and response sensitivity, and an ordinarily skilled practitioner can easily judge and prescribe the dose effective for the desired treatment or prevention. According to a preferable embodiment of the present invention, the daily dose of the pharmaceutical composition of the present invention may be 0.0001-1000 mg/kg.

The pharmaceutical composition of the present invention may be formulated using a pharmaceutically acceptable carrier and/or excipient according to the method that is easily conducted by a person having ordinary skills in the art to which the present invention pertains, and the composition of the present invention may be prepared into a unit dosage form or may be inserted into a multi-dose container. Here, the dosage form may be a solution in a form of an oily or aqueous medium, a suspension, an emulsion, an extract, a powder, granules, a tablet, a capsule, or a gel (e.g., a hydrogel), and may further include a dispersing agent or a stabilizer.

According to another aspect of the present invention, the present invention provides a food composition for an antitussive, expectorant, or anti-inflammatory action, the composition contains, as active ingredients, *Panax ginseng, Adenophora triphylla, Wolfiporia extensa, Rehmannia glutinosa*, and mel.

The composition of the present invention, when prepared as a food composition, contains, in addition to *Panax ginseng, Adenophora triphylla, Wolfiporia extensa, Rehmannia glutinosa*, and mel as active ingredients, the ingredients that are normally added at the time of food manufacturing, for example, proteins, carbohydrates, fats, nutrients, seasonings, and flavoring agents. Examples of the foregoing carbohydrate may include ordinary sugars (monosaccharides, such as glucose and fructose; disaccharides, such as maltose, sucrose and oligosaccharides; and polysaccharides, such as dextrin and cyclodextrin) and sugar alcohols, such as xylitol, sorbitol, and erythritol. Examples of the flavoring agent may include natural flavoring agents (thaumatin, and *stevia* extract (e.g., rebaudioside A, glycyrrhizin, etc.)) and synthetic flavoring agents (saccharin, aspartame, etc.). For example, the food composition of the present invention, when is prepared as a drink, may further contain, in addition to *Panax ginseng, Adenophora triphylla, Wolfiporia extensa, Rehmannia glutinosa*, and mel, citric acid, liquefied fructose, sugar, glucose, acetic acid, malic acid, fruit juice, an *Eucommia ulmoides* extract, a jujube extract, and a licorice extract.

The food composition for an antitussive, expectorant, or anti-inflammatory action may be prepared as a health functional food composition.

The health functional food for an antitussive, expectorant, or anti-inflammatory action contains the ingredients that are ordinarily added at the time of food manufacturing, for example, proteins, carbohydrates, fats, nutrients, and seasonings. For example, the composition, which prepared as a drink, may contain, as an active ingredient, a *hydrangea* tea extract and, as an additional ingredient, a flavoring agent or natural carbohydrate. Examples of the natural carbohydrate include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). Natural flavoring agents (e.g., thaumatin, *stevia* extract, etc.) and synthetic flavoring agents (e.g., saccharin, aspartame, etc.,) may be used as flavoring agents.

Since the food composition for an antitussive, expectorant, or anti-inflammatory action of the present invention is the same as the pharmaceutical composition with respect to an active ingredient, the overlapping descriptions therebetween are omitted to avoid excessive complication of the specification.

According to still another aspect of the present invention, the present invention provides a pharmaceutical composition for preventing or treating a respiratory disease, the composition containing, as active ingredients, *Panax ginseng, Adenophora triphylla, Wolfiporia extensa, Rehmannia glutinosa*, and mel.

As used herein, the term "respiratory disease" refers to respiratory diseases accompanied by symptoms of cough, sputum, or inflammation. The respiratory disease includes asthma, airway infection, cold, and diseases accompanied by cough, bronchospasm, dyspnea, sputum or bronchitis. The airway infection includes at least one upper respiratory tract infection or lower respiratory tract infection selected from the group consisting of acute or chronic rhinitis, sinusitis, laryngopharingitis, otitis media, and bronchitis.

As used herein, the term "prevention" or "preventing" refers to any act that inhibits the respiratory disease or slows the progression of the respiratory disease by administration of the composition of the present invention.

As used herein, the term "treatment" or "treating" refers to the suppression of the development of respiratory disease, the mitigation of respiratory, and the removal of respiratory disease.

According to another aspect of the present invention, the present invention provides a food composition for preventing or alleviating a respiratory disease, the composition containing, as active ingredients, *Panax ginseng, Adenophora triphylla, Wolfiporia extensa, Rehmannia glutinosa*, and mel.

As used herein, the term "alleviation" or "alleviating" refers to any act that ameliorates or favorably change a respiratory disease or disorder by administration of the composition of the present invention.

The food composition for preventing or alleviating a respiratory disease of the present invention is the same as the pharmaceutical composition for an antitussive, expectorant, or anti-inflammatory action with respect to an active ingredient, and is the same as the pharmaceutical composition for preventing or treating a respiratory disease with respect to a target disease, and thus the overlapping descriptions therebetween are omitted to avoid excessive complication of the specification.

According to another aspect of the present invention, the present invention provides a method for alleviating or treating cough, sputum, or an inflammatory disease, the method including administering, to a subject, a composition containing, as active ingredients, *Panax ginseng, Adenophora triphylla, Wolfiporia extensa, Rehmannia glutinosa*, and mel.

According to still another aspect of the present invention, the present invention provides a method for treating a respiratory disease, the method including administering, to a subject, a therapeutically effective amount of a composition containing, as active ingredients, *Panax ginseng, Adenophora triphylla, Wolfiporia extensa, Rehmannia glutinosa*, and mel.

Here, the term "administration" or "administer" is meant that a therapeutically effective amount of the composition of the present invention is directly administered to a subject (subject) in need of the composition, thereby forming the same amount in the body of the subject.

The "therapeutically effective amount" of the composition refers to the content of the composition sufficient to provide a therapeutic or prophylactic effect to a subject to which the composition is to be administered, and the term includes "prophylactically effective amount". In addition, the term "subject" includes, but is not limited to, a human being, mouse, rat, guinea pig, dog, cat, horse, cow, pig, monkey, chimpanzee, beaver, or rhesus monkey. Specifically, the subject of the present invention is a human being.

The method for treating cough, sputum, an inflammatory disease, or a respiratory disease of the present invention is the same as the foregoing composition containing, as active ingredients, *Panax ginseng, Adenophora triphylla, Wolfiporia extensa, Rehmannia glutinosa*, and mel with respect to a composition and a target disease, and thus the overlapping descriptions therebetween are omitted to avoid excessive complication of the specification.

Advantageous Effects

Features and advantages of the present invention are summarized as follows.

(a) The present invention provides a composition for an antitussive, expectorant, or anti-inflammatory action and a composition for preventing, alleviating, or treating a respiratory disease.

(b) The present invention provides a composition having excellent effects compared with an antitussive agent and an expectorant agent.

BRIEF DESCRIPTION OF THE DRAWINGS

FIGS. 1*a*, 1 *b*, 1*c*, 1*d*, 1*e*, and 1*f* show ultra-performance liquid chromatography (UPLC) analysis results of *Adenophora triphylla* (AR), a composition obtained by mixing *Panax ginseng, Wolfiporia extensa, Rehmannia glutinosa*, and mel, without *Adenophora triphylla* (KOG), and a composition obtained by mixing *Adenophora triphylla, Panax ginseng, Wolfiporia extensa, Rehmannia glutinosa*, and mel (SKOG), respectively. FIGS. 1*a*, 1*c* and 1*e* show UPLC analysis results of standard materials.

DETAILED DESCRIPTION

Figure 1A:
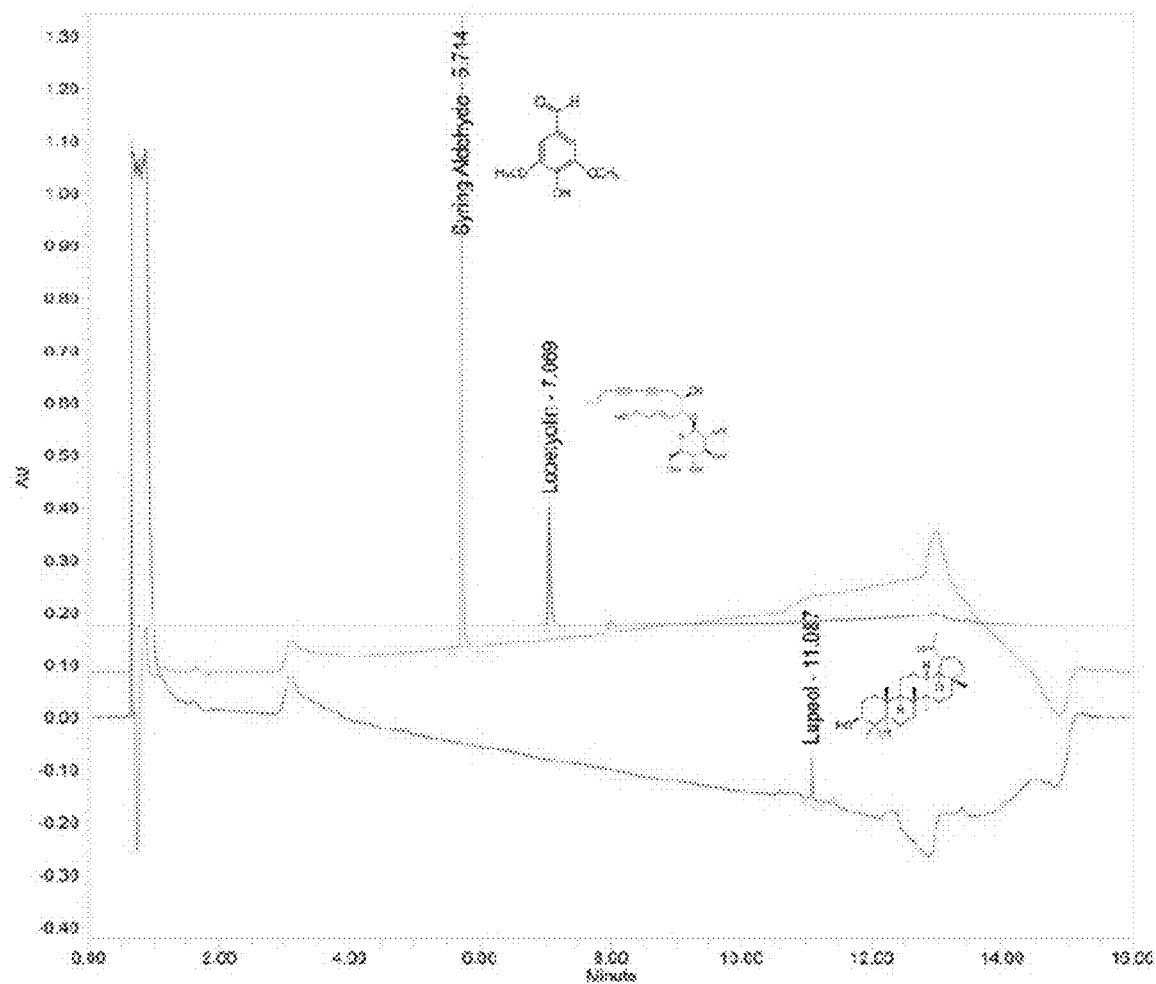

Hereinafter, the present invention will be described in detail with reference to examples. These examples are only for illustrating the present invention more specifically, and it would be obvious to those skilled in the art that the scope of the present invention is not limited by these examples.

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Example 1. Preparation of Composition for Antitussive, Expectorant, And Anti-Inflammatory Actions (1) Materials Pale yellow *Adenophora triphylla* Radix (AR, Andong, Gyeongsangbukdo, Korea), *Panax ginseng* (Geumsan, Chungcheongnamdo, Korea), *Wolfiporia extensa* (Anhui, Chinese), *Rehmannia glutinosa* (Andong and Gunwi, Gyeongsangbukdo, Korea), and mel (Okcheon, Chungcheongbukdo, Korea) were received from Okcheon Dang Pharmaceutical Co., Ltd. (Yeongcheon, Korea). Some test materials were stored in Medical Research center for Globalization of Herbal Formulation, Daegu Haany University, Gyeongsan, Korea) (Code No. *Adenophora triphylla*-AR2016Ku01, KOG-KOG2016Ku01, SKOG-SKOG2016Ku01). In addition, theobromine (TB, white powder), ambroxol (AM, white powder), and dexamethasone (DEXA, white granules) were purchased from Sigma-Aldrich (USA). AR and the above three kinds of control drugs were stored at 4° C. in a refrigerator until use.

(2) Preparation Method for *Adenophora triphylla* Sample

*Adenophora triphylla* was washed to remove impurities, such as soil, followed by complete removal of moisture, and then dried at 90-120° C. for 5-8 hours by constant hot-air drying or other drying methods, to a final moisture content of 5% or less. The dried product was prepared into a powder having a particle size of 80 mesh or more by using a pulverizer, such as a pin mill, a ball mill, a rod mill, an air mill, or a jet mill.

(3) Preparation Method for KOG

*Wolfiporia extensa* was washed to remove impurities, such as soil, followed by removal of moisture, and then the surface thereof was completely dried. *Panax ginseng* was washed against impurities, such as soil, to remove moisture, and then dried at 90-120° C. for 5-8 hours by hot-air drying or other drying methods, to a final moisture content of 5% or less. The dried *Wolfiporia extensa* and *Panax ginseng* were prepared into a powder having a particle size of 80 mesh or more by using a pulverizer, such as a pin mill, a ball mill, a rod mill, an air mill, or a jet mill. *Rehmannia glutinosa* was washed to remove impurities, such as soil, followed by removal of moisture, pulverized through a mechanical pulverizer, such as a blender, and then passed through a net or a filter with 70-80 mesh through a mechanical juicing device, such as a hydraulic presser to obtain a juice thereof. The juice needs to have a sugar content of 15-18 brix and a solid content of 13-16%, and needs to have a yield of 70% or more in the process of obtaining the juice through pulverization. Mel was processed to have a moisture content of 22-24% by heating at 80-85° C. KOG was prepared by mixing 4-5 wt % of the obtained *Panax ginseng* powder, 8-10 wt % of the *Wolfiporia extensa* powder, 4-5 wt % of the *Adenophora triphylla* powder, 35-40 wt % of mel, and 43-48 wt % of the *Rehmannia glutinosa* juice, followed by first aging at 94.5-96.5° C. for 72 hours, first cooling at 8-12° C. for 24 hours, second aging at 94.5-96.5° C. for 24 hours, and second cooling at room temperature for 72 hours.

(4) Preparation Method for SKOG

*Wolfiporia extensa*, *Panax ginseng*, *Rehmannia glutinosa*, and mel were prepared in the same manner as in the preparation method for KOG described above. *Adenophora triphylla* was washed against impurities, such as soil, to remove moisture, and then dried at 90-120° C. for 5-8 hours by hot-air drying or other drying methods, to a final moisture content of 5% or less. The dried product was prepared into a powder having a particle size of 80 mesh or more by using a pulverizer, such as a pin mill, a ball mill, a rod mill, an air mill, or a jet mill.

SKOG was prepared by mixing 4-5 wt % of the obtained *Panax ginseng* powder, 8-10 wt % of the *Wolfiporia extensa* powder, 4-5 wt % of the *Adenophora triphylla* powder, 35-40 wt % of mel, and 43-48 wt % of the *Rehmannia glutinosa* juice, followed by first aging at 94.5-96.5° C. for 72 hours, first cooling at 8-12° C. for 24 hours, second aging at 94.5-96.5° C. for 24 hours, and second cooling at room temperature for 72 hours or more.

Example 2. Analysis of Specific Ingredients of AR, KOG and SKO (1) Instrument and Reagent Waters ACQUITY™ ultra performance liquid chromatography system (Waters Corporation, Milford, Mass., USA) equipped with Waters ACQUITY™ photodiode array detector (PDA; Waters Corporation, Milford, Mass., USA) and Waters ACQUITY™ BEH C18 column (1.7 μm, 2.1×100; Waters Corporation, Milford, Mass., USA) was used in ultra performance liquid chromatography (UPLC) analysis. In addition, Empower (Waters Corporation, Milford, Mass., USA) was used as analysis software, in the current analysis. A sample extractor was ultrasonicator model 8210R-DHT (Branson Ultrasonics, Danbury, Conn.). Reagents for this experiment were methanol (HPLC grade, Junsei Chemical Co., Ltd., Tokyo, Japan), acetonitrile (HPLC grade, BAKER, Center Valley, Pa., USA), and then water (Tertiary distilled water). The standard preparations of this experiment were from the Sigma-Aldrich (St. Louise, Mo., USA) or Extrasynthese (Genay Cedex, France).

(2) Preparation of the Standard Solution

The amount preparations of AR contain materials (lupeol, lobetyolin and syring aldehyde), Rehmanniae Radix Crudus contain materials (acteoside, catalposide and 5-hydroxymethyl-2-furfural (5H2F)) and *Ginseng* Radix Alba contain materials (ginsenoside Rg3 (Rg3)) were measured accurately and melted by DMSO (in lupeol) or methanol (in lobetyolin, syring aldehyde, acteoside, catalposide, 5H2F and Rg3) for standard stock solution as concentration level of 1 μg/ml. In the next, the right amounts of the standard undiluted solution were diluted with the methanol to be contained 1, 5, 10 ng/ml and they were a standard solution. A standard curve determination coefficient ($R^2$) value of all standard materials was more than 0.999.

(3) Preparation of the Test Liquid for Quantitative Analysis

A test liquid for quantitative analysis was mixed with the sample equally and was measured 1 g precisely, and was added on the 30% methanol 10 ml, and then was extracted by microwave for 1 hour. This test liquid was filtered from the membrane filter of below 0.2 μm diameter, and was picked out as the test liquid.

(4) Quantitation of the Ingredients

The amounts of lupeol, lobetyolin, syring aldehyde acteoside, catalposide, 5H2F and Rg3 in AR, KOG or SKOG were quantified using UPLC equipped with PDA (photodiode array detector) and BEH (bridged ethylene hybrid) C18 column, and the Empower software. A temperature of the column was analyzed at the room temperature. In case of the PDA analysis wavelength, lupeol, acteoside, catalposide and 5H2F were analyzed in 280 nm, lobetyolin was analyzed in 310 nm, and then syring aldehyde was analyzed in 254 nm, respectively. A mobile phase was a mixed liquid of the acetonitrile and water which contain 0.1% formic acids as follows.

TABLE 1

| Time (min) | 0.1% FA/Water (%) | 0.1% FA/Acetonitrile (%) | Flow rate (ml/min) |
| --- | --- | --- | --- |
| 0 | 98 | 2 | 0.40 |
| 1.0 | 98 | 2 | 0.40 |
| 2.0 | 90 | 10 | 0.40 |
| 4.0 | 70 | 30 | 0.40 |
| 7.0 | 50 | 50 | 0.40 |
| 9.0 | 30 | 70 | 0.40 |
| 10.0 | 10 | 90 | 0.40 |
| 12.0 | 0 | 100 | 0.40 |
| 14.0 | 98 | 2 | 0.40 |
| 16.0 | 98 | 2 | 0.40 |

Rg3 was analyzed in 203 nm and the mobile phase was a mixed liquid of the acetonitrile and water as follows.

TABLE 2

| Time (min) | Water (%) | Acetonitrile (%) | Flow rate (ml/min) |
| --- | --- | --- | --- |
| 0 | 85 | 15 | 0.40 |
| 1.0 | 85 | 15 | 0.40 |
| 14.0 | 70 | 30 | 0.40 |
| 15.0 | 68 | 32 | 0.40 |
| 16.0 | 60 | 40 | 0.40 |
| 17.0 | 45 | 55 | 0.40 |
| 19.0 | 45 | 55 | 0.40 |
| 21.0 | 10 | 90 | 0.40 |
| 22.0 | 10 | 90 | 0.40 |
| 23.0 | 85 | 15 | 0.40 |

The analysis condition was as in the following. The sample was injected with 2 μl, and a flow rate was 0.4 ml/min, and the result of analysis was observed qualitative checking by retention time, and then was quantified by peak area method (Table 3 and FIG. 1a to 1f).

TABLE 3

| Test materials Ingredient (mg/kg) | AR | KOG | SKOG |
| --- | --- | --- | --- |
| Lupeol | 6.99 ± 0.24 | — | 224.52 ± 12.5 |
| Lobetyolin | 2029.00 ± 1.96 | — | — |
| Syring aldehyde | 0.26 ± 0.03 | — | 0.14 ± 0.01 |
| 5H2F | — | 628.26 ± 13.2 | 559.50 ± 1.70 |
| Acteoside | — | 0.33 ± 0.02 | 0.31 ± 0.01 |
| Catalposide | — | 0.41 ± 0.03 | 0.33 ± 0.01 |
| Rg3 | — | 7.27 ± 0.46 | 4.42 ± 0.02 |

Figure 1B:
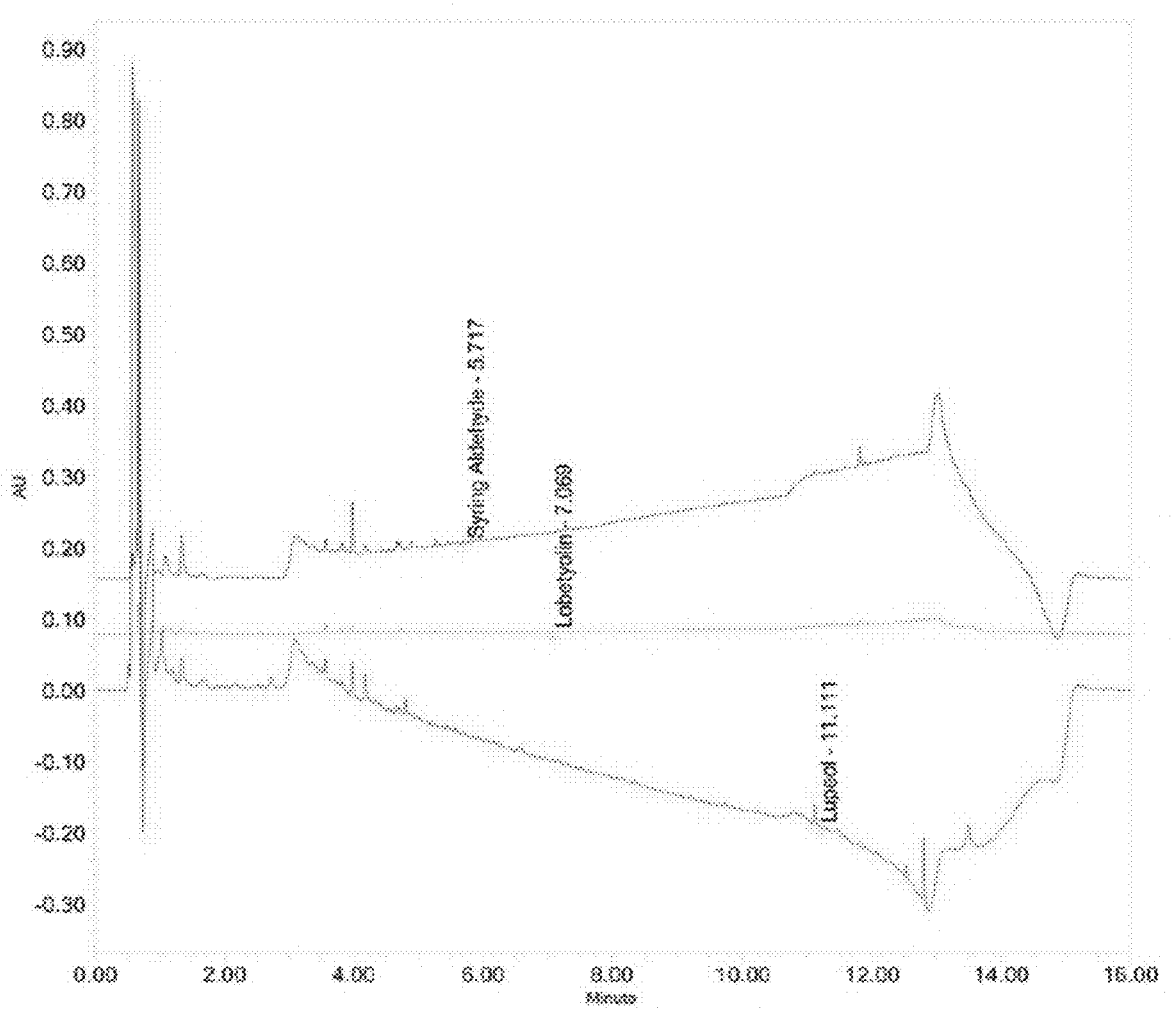
FIGS. 1*b*, 1*d* and 1*f* show UPLC analysis results of AR, KOR and SKOG, respectively.
Figure 1C:
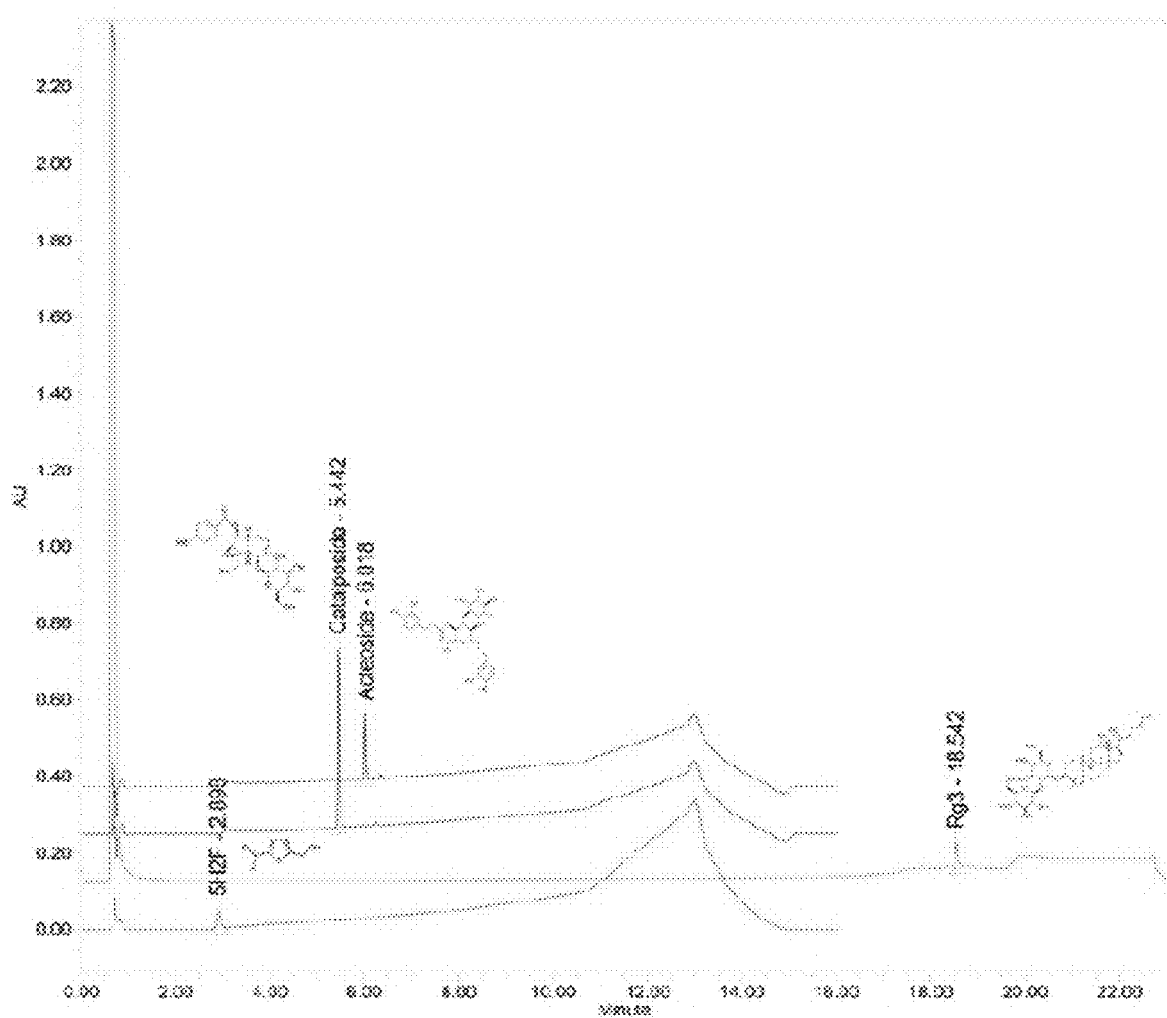
Figure 1D:
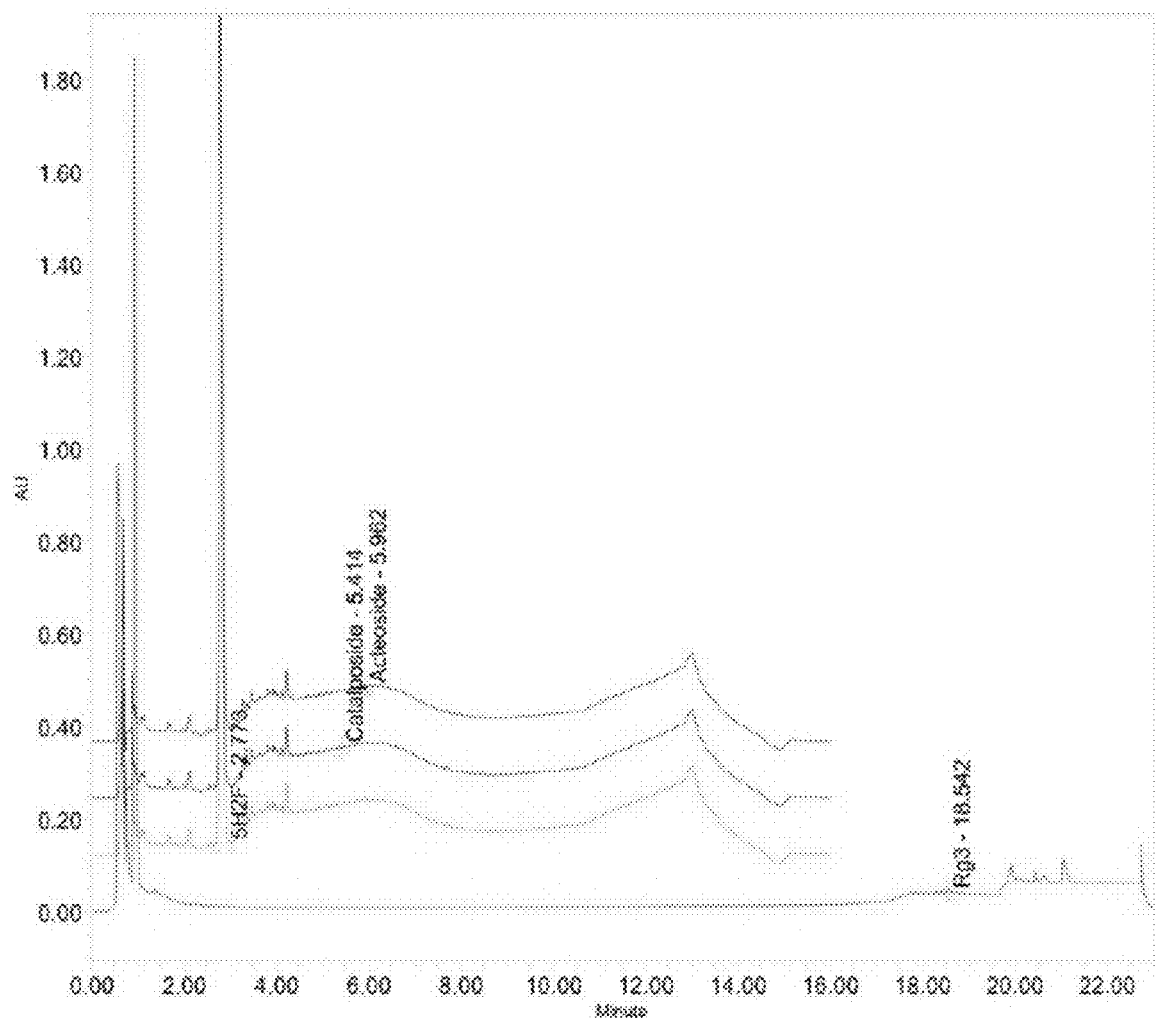
Figure 1E:
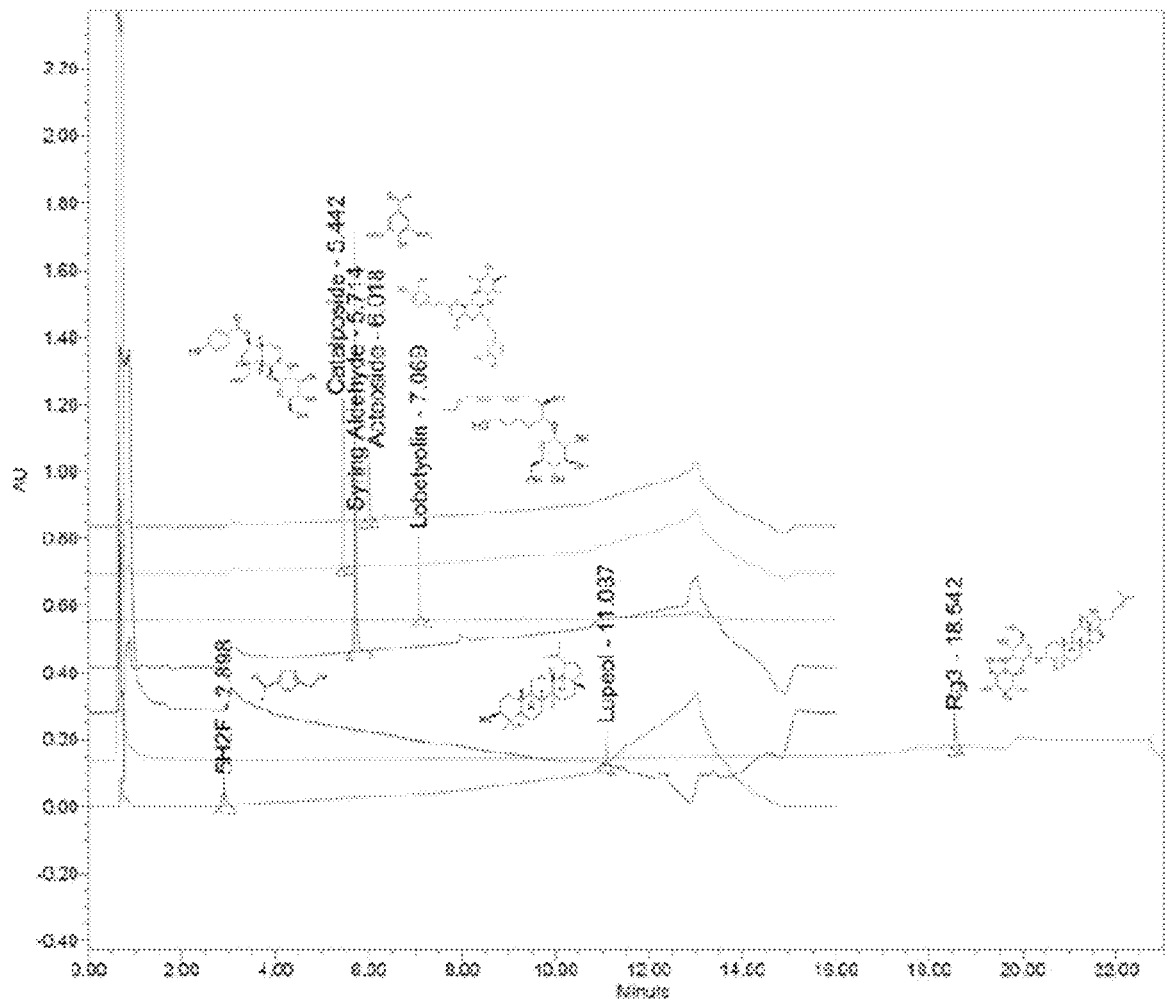
Figure 1F:
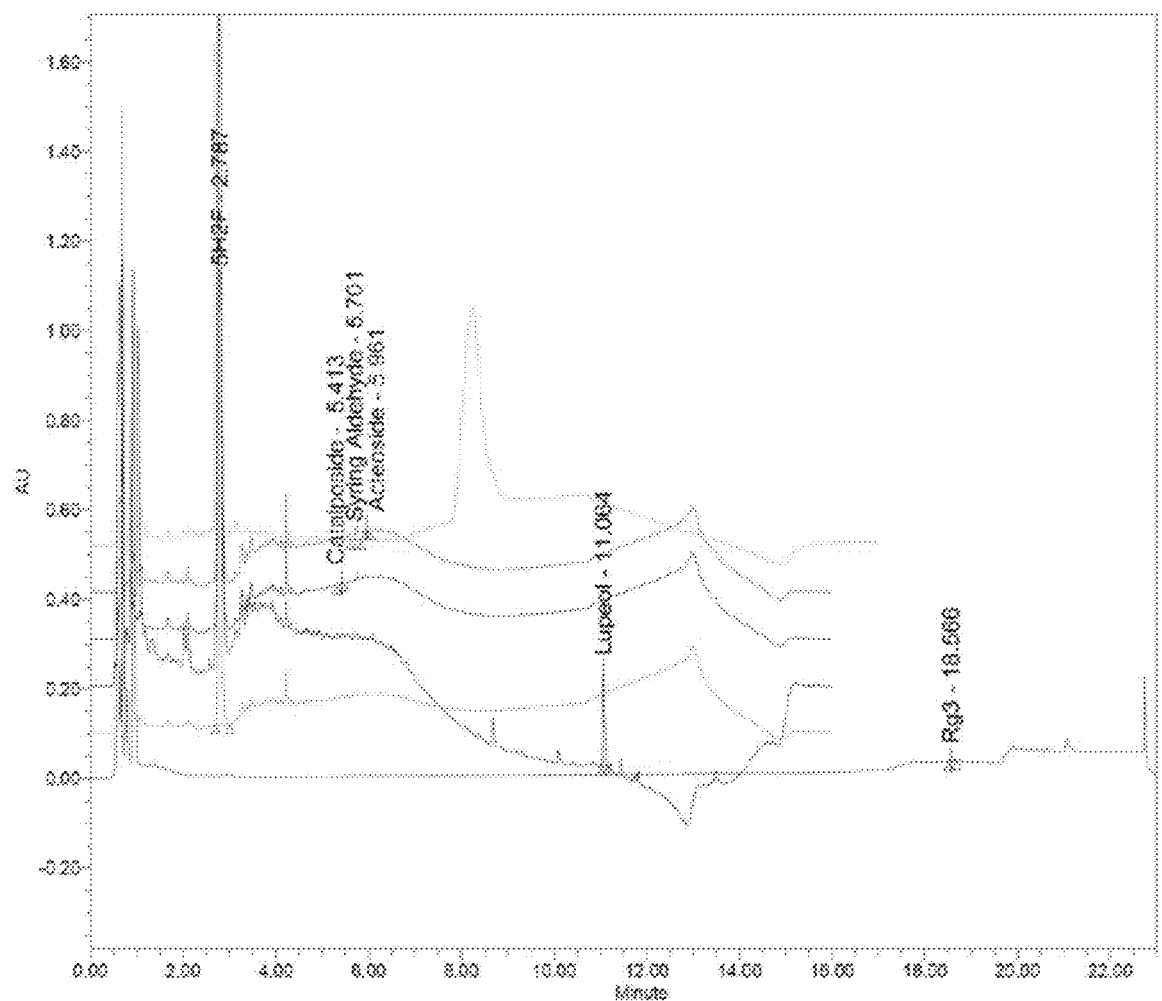

FIGS. 1b, 1d and 1d show UPLC analysis results of AR, KOG and SKOG, respectively.

Lupeol, lobetyolin and syring aldehyde were detected as 6.99±0.24, 2029.00±1.96 and 0.26±0.03 mg/kg in AR, 5-hydroxymethyl-2-furfural (5H2F), acteoside, catalposide and Ginsenoside-Rg3 (Rg3) were detected as 628.26±13.2, 0.33±0.02, 0.41±0.03 and 7.27±0.46 mg/kg in KOG, and lupeol, syring aldehyde, 5H2F, acteoside, catalposide and Rg3 were detected as 224.52±12.5, 0.14±0.01, 559.50±1.70, 0.31±0.01, 0.33±0.01 and 4.42±0.02 mg/kg in SKOG, used in this study at UPLC analysis, respectively (Table 1 and FIGS. 1a to 1f).

Example 3. Antitussive Assay (1) Animals and Husbandry

One-hundred thirty two 6-week male SPF/VAF CrljOri: CD1 [ICR] mice (OrientBio, Seungnam, Korea; body weight ranged in 29-32 g upon receipt) were prepared, and eight groups of 10 mice each were selected based on the body weights at 7 days after acclimatization based on the body weights (intact control: 34.30±1.74 g, ranged in 31.8-37.0 g; $NH_4OH$ treated mice: 34.17±1.32 g, ranged in 31.0-37.3 g), as follows.

Animals were allocated four per polycarbonate cage in a temperature (20-25° C.) and humidity (50-55%) controlled room. Light:dark cycle was 12 hour: 12 hour, and s standard rodent chow (Cat. No. 38057; Purina feed, Seungnam, Korea) and water were supplied free to access. All laboratory animals were treated according to the national regulations of the usage and welfare of laboratory animals, and approved by the Institutional Animal Care and Use Committee in Daegu Haany University (Gyeongsan, Gyeongbuk, Korea) [DHU2016-034, Apr. 22, 2016; ANNEX III].

Experimental groups (Eight groups, 10 mice in each group were finally sacrificed)

1. Intact vehicle control: Vehicle (distilled water) treated intact control mice
2. NH$_4$OH control: Vehicle administered and NH$_4$OH exposed control mice
3. TB: TB 50 mg/kg administered and NH$_4$OH exposed mice
4. AR: AR 400 mg/kg administered and NH$_4$OH exposured mice
5. KOG: KOG 400 mg/kg administered and NH$_4$OH exposured mice
6. SKOG400: SKOG 400 mg/kg administered and NH$_4$OH exposured mice
7. SKOG200: SKOG 200 mg/kg administered and NH$_4$OH exposured mice
8. SKOG100: SKOG 100 mg/kg administered and NH$_4$OH exposured mice (2) Test Substance Administration SKOG were suspended in distilled water as 40, 20 and 10 mg/ml concentration, and orally administered in a volume of 10 ml/kg (as equivalence to 400, 200 and 100 mg/kg), once a day for 11 days before NH$_4$OH exposure. In addition, AR and KOG were also suspended in distilled water as 40 mg/ml concentration, and orally administered in a volume of 10 ml/kg (as equivalence to 400, 200 and 100 mg/kg), once a day for 11 days before NH$_4$OH exposure. TB was also dissolved in distilled water as 5 mg/ml concentrations, and also orally administered in a volume of 10 ml/kg (as equivalence to 50 mg/kg), once a day for 11 days before NH$_4$OH exposure. In intact vehicle and NH$_4$OH control mice, distilled water 10 ml/kg was orally administered, instead of AR, KOG, SKOG or TB to provide same restrain stresses, in the present experiment.

(3) Body Weight Measurements

Changes of body weight were measured at once a day from 1 day before initial to end of last 11th oral administration of AR, KOG, SKOG or TB using an automatic laboratory animal weighing electronic balance (Precisa Instrument, Dietikon, Switzland). Animals were overnight fasted (about 18 hours, water was not restricted) before initial test substance administration and sacrifice to reduced individual differences from feeding, and also to reduce the individual body weight differences at start of experiment, the body weight gains during 11 days of oral administration of AR, KOG, SKOG or TB were calculated as follow Equation [1], in the current experiment.

Body weight gains during 11 days of oral administration of test substances[$B-A$]=Body weights at last administration[$B$]−Body weights at first administration[$A$]  Equation [1]

Figure 2:
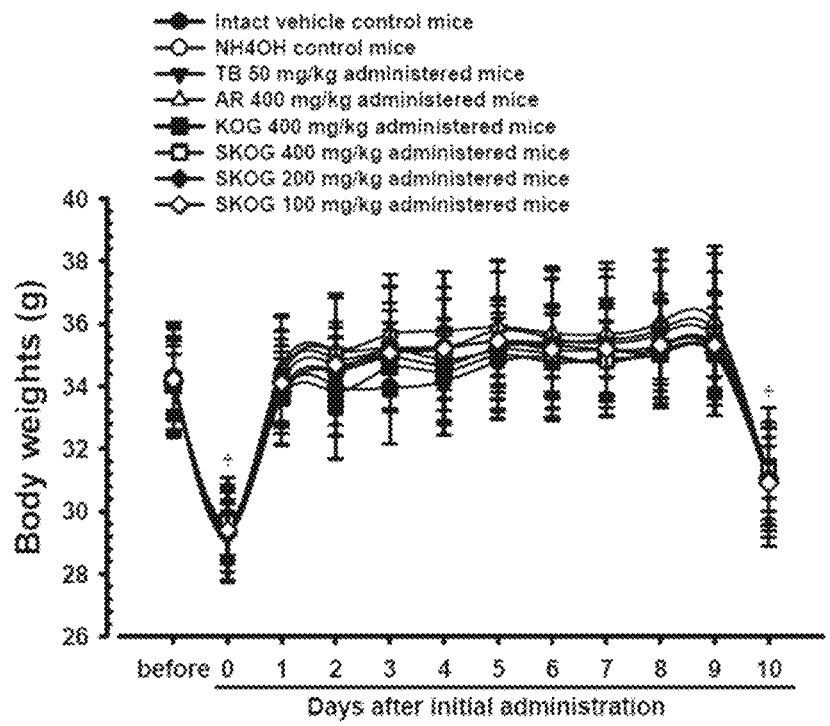
FIG. 2 is a graph showing the body weight change of experimental animals in the antitussive effect measurement by SKOG administration.

The results are shown in Table 4 and FIG. 2.

TABLE 4

| Periods | Body weights (g) at test material administration | | Body weight gains (g) |
|---|---|---|---|
| Groups | First [A] | Last [B] | [B − A] |
| Controls | | | |
| Intact | 29.34 ± 1.29 | 30.98 ± 1.39 | 1.64 ± 0.74 |
| NH$_4$OH | 29.44 ± 1.65 | 31.11 ± 2.22 | 1.67 ± 0.84 |

TABLE 4-continued

| Periods | Body weights (g) at test material administration | | Body weight gains (g) |
|---|---|---|---|
| Groups | First [A] | Last [B] | [B − A] |
| Reference | | | |
| TB 50 mg/kg | 29.23 ± 1.49 | 30.94 ± 1.77 | 1.71 ± 0.97 |
| AR 400 mg/kg | 29.41 ± 0.96 | 31.12 ± 1.74 | 1.71 ± 1.18 |
| KOG 400 mg/kg | 29.58 ± 1.24 | 31.10 ± 1.56 | 1.52 ± 0.61 |
| SKOG | | | |
| 400 mg/kg | 29.66 ± 1.07 | 31.35 ± 1.34 | 1.69 ± 0.70 |
| 200 mg/kg | 29.27 ± 0.75 | 31.04 ± 0.62 | 1.77 ± 0.32 |
| 100 mg/kg | 29.41 ± 0.86 | 30.92 ± 1.17 | 1.51 ± 0.88 |

FIG. 2 shows the weight change of the animals of antitussive effect measurement by SKOG administration.

As shown in Table 4 and FIG. 2, No significant changes on the body weights and gains during 11 days of continuous oral administration periods were detected in NH$_4$OH control mice as compared with those of intact vehicle control mice, respectively. In addition, no significant changes on the body weights and gains were demonstrated in all AR and KOG 400 mg/kg, TB 50 mg/kg, SKOG 400, 200 and 100 mg/kg treated mice as compared with those of NH$_4$OH control mice, and no significant changes on the body weights and gains were also demonstrated in SKOG 400, 200 and 100 mg/kg treated mice as compared to those of AR and KOG 400 mg/kg, in the current study.

The body weight gains during 11 days of continuous oral administration periods in NH$_4$OH control were changed as 1.83% as compared with intact vehicle control, and they were changed as 2.40, 2.40, −8.98, 1.20, 5.99 and −9.58% in TB 50 mg/kg, AR and KOG 400 mg/kg, SKOG 400, 200 and 100 mg/kg oral administered mice as compared with those of NH$_4$OH control mice, respectively.

(4) Coughing Inducement and Monitoring

Coughing was induced by single inhalation of 25% NH$_4$OH (Sigma-Aldrich, St. Louise, Mo., USA) 0.3 ml in 1,000 ml glass Erlenmeyer flask for 45 sec at 1 hour after last 11th test substance administration, individually. After NH$_4$OH exposure, the numbers of coughing responses were measured during 6 min using video observation equipments, as described previously with some modifications. Individual intact vehicle control mouse was exposed to 0.3 ml of saline contained 1,000 ml glass Erlenmeyer flask for 45 sec, instead of NH$_4$OH, in this experiment. The criteria to define cough in mice is that opening the mouth accompanying sound of coughing, contraction of thoracic and abdomen muscles, and a jerking of the front body.

Figure 3:
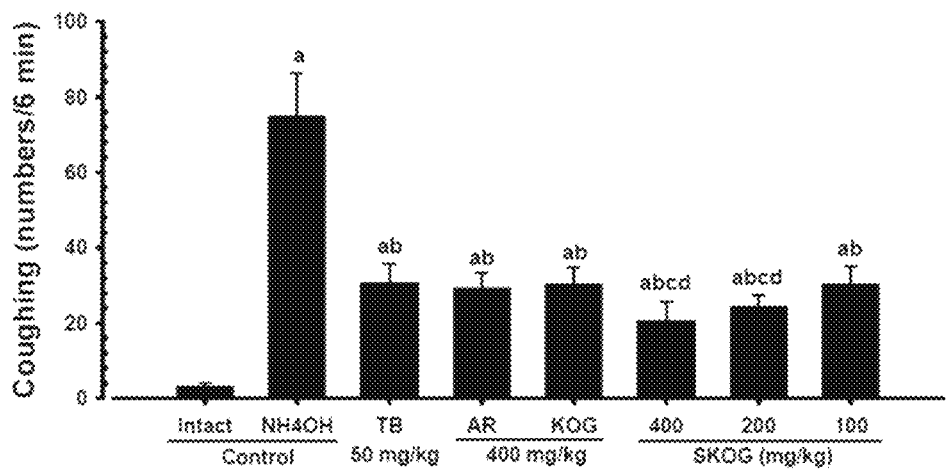
FIG. 3 is a graph showing the coughing number change of experimental animals by SKOG administration.

FIG. 3 is a graph showing the change in the number of coughs in an experimental animal in the measurement of the antitussive effect by administration of SKOG.

Significant ($p<0.01$) increases of the numbers of coughing responses during 6 min after 45 sec exposure of NH$_4$OH in NH$_4$OH control mice as compared with intact vehicle control mice. However, significant ($p<0.01$) and dose-dependent decreases of coughing responses were observed in SKOG 400, 200 and 100 mg/kg as compared with those of NH$_4$OH control mice, respectively. In addition, AR and KOG 400 mg/kg, TB 50 mg/kg treated mice also showed significant ($p<0.01$) decreases of the numbers of coughing responses as compared with those of NH$_4$OH control mice, respectively. Especially, SKOG 400 and 200 mg/kg showed significantly ($p<0.01$) decreased coughing numbers as compared with those of AR and KOG 400 mg/kg, and SKOG 100 mg/kg showed similar favorable inhibitory effects on the NH$_4$OH-induced coughing responses as compared with those of AR and KOG 400 mg/kg, respectively. In addition, AR and KOG 400 mg/kg, SKOG100 mg/kg showed similar or more favorable inhibitory effects on the NH4OH-induced coughing responses as compared to those of TB 50 mg/kg, in the present study (FIG. 3).

Mean numbers of coughing responses during 6 min after 45 sec exposure of NH$_4$OH in NH$_4$OH control were changed as 2390.00% as compared with intact vehicle control, but they were changed as −59.04, −60.91, −59.71, −72.42, −67.34 and −59.57% in TB 50 mg/kg, AR and KOG 400 mg/kg, SKOG 400, 200 and 100 mg/kg oral administered mice as compared with those of NH$_4$OH control mice, respectively.

(5) Histopathology

After video image acquirement, some parts of individual lung (left lateral lobes) and trachea (3 mm from thyroid cartilages) were sampled and fixed in 10% neutral buffered formalin (NBF), and crossly trimmed. Then embedded in paraffin, sectioned (3~4 μm) and stained with Hematoxylin and eosin (H&E) for general histopathology or toluidine blue for mast cells, and after that the histopathological profiles of each sample were observed under light microscope (Model Eclipse 80i, Nikon, Tokyo, Japan). To more detail changes, mean diameters of trachea lumen (μm), thicknesses of trachea wall, epithelium and submucosa (μm), numbers of infiltrated inflammatory cells and mast on the trachea (cells/mm$^2$), mean alveolar surface area (ASA; %/mm$^2$), mean thicknesses of alveolar septum (μm), numbers of infiltrated inflammatory cells on the alveolar septum (cells/mm2) were analyzed using a computer-assisted image analysis program (iSolution FL ver 9.1, IMT i-solution Inc., Quebec, Canada), according to previously established methods, respectively. The histopathologist was blinds to group distribution when this analysis was made, and at least five repeated measurements in same histological specimens prepared were considered to calculate each mean histomorphometrical value, whenever possible, in this histopathological evaluation (FIG. 4).

Figure 4:
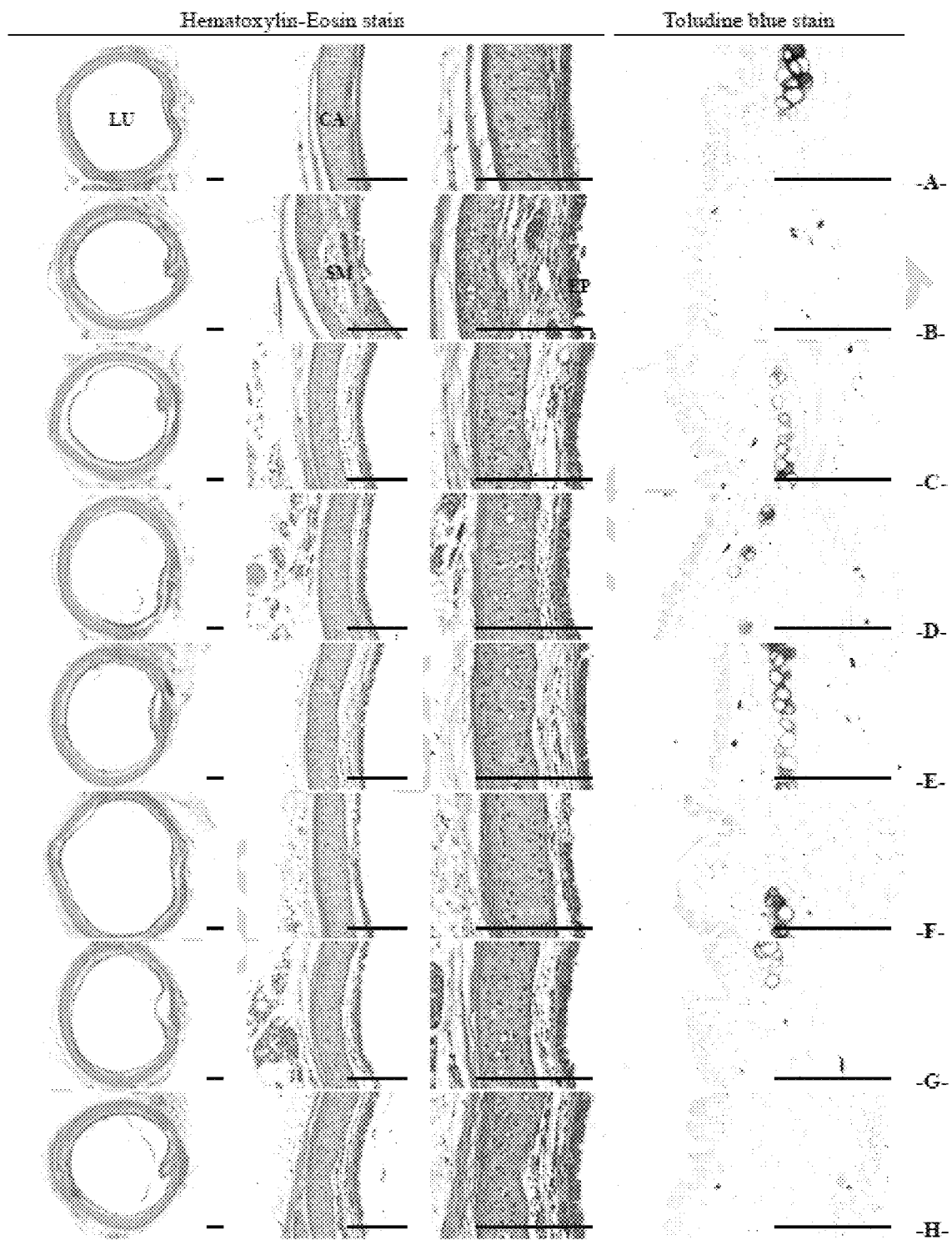
FIG. 4 shows the histopathological change of the organs of experimental animals by SKOG administration. Left regions indicate Hematoxylin-Eosin stain results and right regions indicate toluidine blue stain results. "LU", "CA", "CM", and "EP" represent lumen, cartilage, submucosa, and epithelium, respectively. A: normal control group, B: NH$_4$OH control group, C: TB 50 mg/kg administered group, D: AR 400 mg/kg administered group, E: KOG 400 mg/kg administered group, F: SKOG 400 mg/kg administered group, G: SKOG 200 mg/kg administered group, H: SKOG 100 mg/kg administered group. Scale bars indicate 120 μm.
Figure 5:
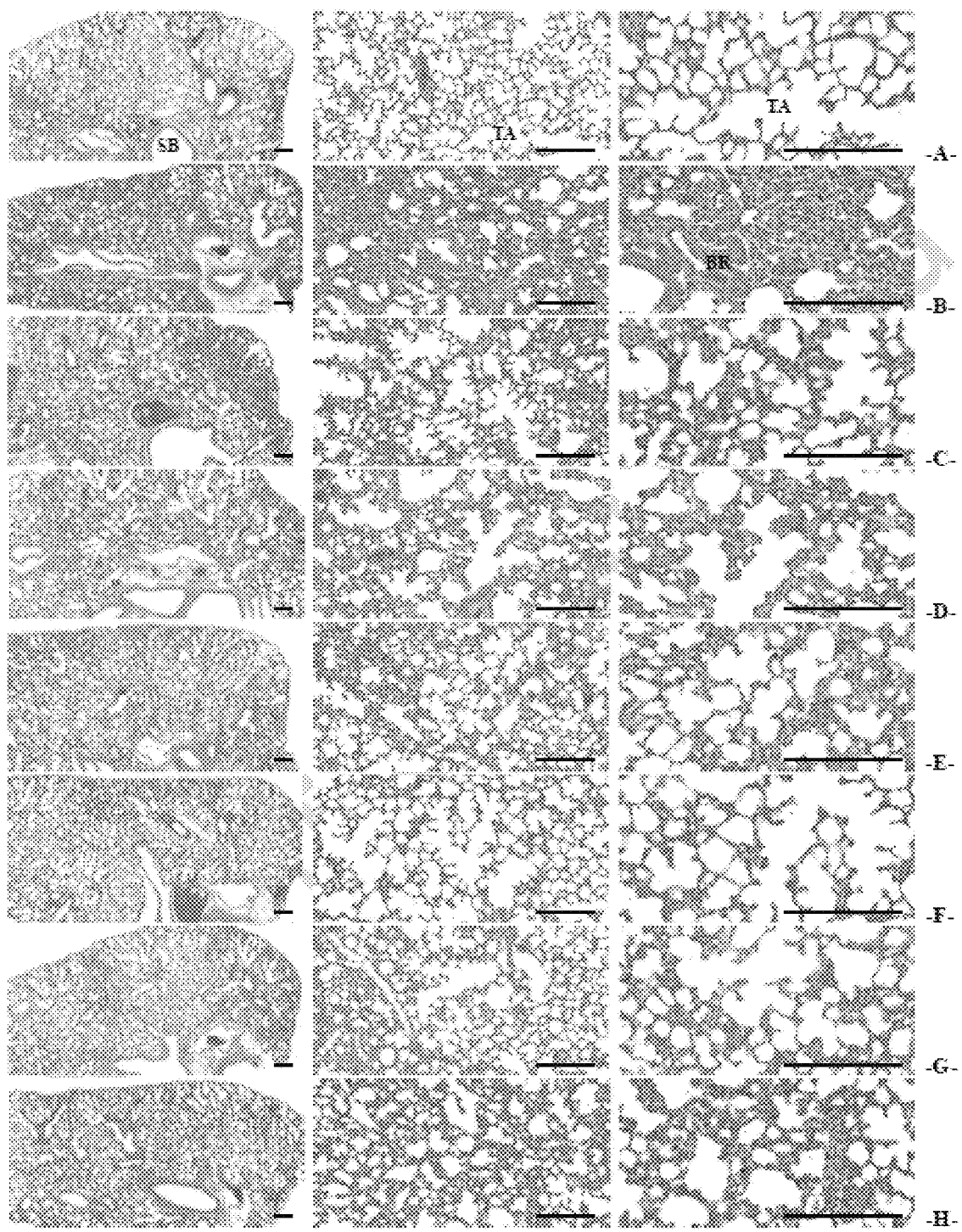
FIG. 5 shows the histopathological change of the lungs of experimental animals by SKOG administration. "SB", "TA", and "BR" represent secondary bronchus, alveolus-terminal bronchiole, and bronchus, respectively. A: normal control group, B: NH$_4$OH control group, C: TB 50 mg/kg administered group, D: AR 400 mg/kg administered group, E: KOG 400 mg/kg administered group, F: SKOG 400 mg/kg administered group, G: SKOG 200 mg/kg administered group, H: SKOG 100 mg/kg administered group. Scale bars indicate 120 μm.

The results are shown in Tables 5 and 6, and FIGS. 4 and 5.

TABLE 6

| Index Groups | Alveolar surface area (%) | Septum thickness (μm) | inflammatory cells (numbers/mm$^2$) |
|---|---|---|---|
| Controls | | | |
| Intact | 78.87 ± 9.31 | 7.32 ± 1.45 | 30.20 ± 19.63 |
| NH$_4$OH | 30.94 ± 9.58$^a$ | 72.41 ± 10.80$^g$ | 1886.70 ± 394.17$^g$ |
| Reference | | | |
| TB 50 mg/kg | 51.13 ± 5.95$^{ac}$ | 30.53 ± 10.06$^{gh}$ | 492.00 ± 114.18$^{gh}$ |
| AR 400 mg/kg | 53.83 ± 7.88$^{ac}$ | 27.22 ± 7.28$^{gh}$ | 453.80 ± 104.35$^{gh}$ |
| KOG 400 mg/kg | 52.34 ± 8.24$^{ac}$ | 27.98 ± 3.75$^{gh}$ | 492.60 ± 118.49$^{gh}$ |
| SKOG | | | |
| 400 mg/kg | 71.32 ± 5.65$^{bcdf}$ | 12.56 ± 2.52$^{ghik}$ | 234.20 ± 42.55$^{ghik}$ |
| 200 mg/kg | 62.29 ± 6.45$^{acef}$ | 20.26 ± 3.12$^{ghik}$ | 347.60 ± 79.19$^{ghik}$ |
| 100 mg/kg | 53.36 ± 9.65$^{ac}$ | 27.99 ± 6.85$^{gh}$ | 481.90 ± 132.69$^{gh}$ |

Values are expressed mean ± SD of 10 mice.

FIGS. 4 and 5 show the histopathological change of the organs and lung of experimental animals by SKOG administration, respectively.

Significant ($p<0.01$) decreases of the diameters of trachea lumen, increases of trachea wall total, epithelium and submucosa thicknesses, the numbers of trachea infiltrated inflammatory and mast cells, decreases of ASA, increases of the alveolar septum thicknesses and the numbers of inflammatory cells between alveolar septum were observed in the trachea and lung of NH$_4$OH control as classic allergic acute inflammation related histopathological findings. However, these NH$_4$OH-induced allergic acute inflammation related histopathological findings were significantly ($p<0.01$) and dose-dependently inhibited by 11 days of continuous oral pretreatment of SKOG 400, 200 and 100 mg/kg as compared with those of NH$_4$OH control mice, respectively. In addition, AR and KOG 400 mg/kg, TB 50 mg/kg also significantly ($p<0.01$) reduced the NH$_4$OH-induced allergic acute inflammation related histopathological findings as compared with those of NH4OH control mice, respectively. Especially, SKOG400 and 200 mg/kg showed significantly ($p<0.01$ or $p<0.05$) decreased NH$_4$OH-induced allergic acute inflam-

TABLE 5

| Groups | Diameter of lumen (μm) | Thickness (μm) Total wall | Epithelium | Submucosa | Cells (Numbers/mm$^2$) Inflammatory | Mast |
|---|---|---|---|---|---|---|
| Control | | | | | | |
| Intact | 1177.86 ± 13.95 | 161.47 ± 15.34 | 14.38 ± 2.91 | 26.60 ± 4.85 | 21.40 ± 12.21 | 1.20 ± 0.79 |
| NH$_4$OH | 658.57 ± 106.44$^a$ | 220.38 ± 13.45$^h$ | 37.53 ± 9.43$^h$ | 89.73 ± 10.46$^h$ | 449.30 ± 102.75$^h$ | 38.70 ± 11.66$^h$ |
| Reference | | | | | | |
| TB 50 mg/kg | 860.11 ± 100.75$^{ac}$ | 191.23 ± 10.24$^{hi}$ | 24.21 ± 4.36$^{hi}$ | 47.31 ± 11.39$^{hi}$ | 167.40 ± 40.26$^{hi}$ | 14.30 ± 4.60$^{hi}$ |
| AR 400 mg/kg | 934.14 ± 104.43$^{dc}$ | 185.59 ± 10.94$^{hi}$ | 23.07 ± 3.32$^{hi}$ | 44.99 ± 6.09$^{hi}$ | 162.70 ± 37.57$^{hi}$ | 8.60 ± 2.27$^{hi}$ |
| KOG 400 mg/kg | 934.89 ± 83.13$^{ac}$ | 186.21 ± 11.10$^{hi}$ | 23.87 ± 2.38$^{hi}$ | 40.31 ± 6.64$^{hi}$ | 134.10 ± 20.32$^{hi}$ | 8.40 ± 1.51$^{hi}$ |
| SKOG | | | | | | |
| 400 mg/kg | 1087.76 ± 118.72$^{bcdf}$ | 171.56 ± 7.07$^{hikm}$ | 18.92 ± 2.14$^{hikm}$ | 30.30 ± 3.24$^{lkm}$ | 85.50 ± 19.82$^{hikm}$ | 1.30 ± 1.03$^{ikm}$ |
| 200 mg/kg | 1036.55 ± 84$^{aceg}$ | 175.45 ± 5.03$^{hikm}$ | 19.74 ± 1.37$^{hikm}$ | 32.71 ± 3.79$^{hikm}$ | 120.70 ± 20.94$^{hikm}$ | 3.70 ± 1.34$^{hikm}$ |
| 100 mg/kg | 936.74 ± 70.89$^{ac}$ | 185.19 ± 7.57$^{hi}$ | 23.76 ± 3.34$^{hi}$ | 42.41 ± 8.60$^{hi}$ | 177.60 ± 26.02$^{hi}$ | 8.70 ± 2.16$^{hi}$ |

Values are expressed mean ± SD of 10 mice mation related histopathological findings as compared with those of AR and KOG 400 mg/kg, and SKOG 100 mg/kg showed similar favorable inhibitory effects on the NH$_4$OH-induced allergic acute inflammation related histopathological findings as compared with those of AR and KOG 400 mg/kg, respectively. In addition, AR and KOG 400 mg/kg, SKOG 100 mg/kg showed similar or more favorable inhibitory effects on the NH$_4$OH-induced allergic acute inflammation related histopathological findings as compared to those of TB 50 mg/kg, in this study (Tables 5 and 6, FIGS. 4 and 5).

Mean diameters of trachea lumen in NH$_4$OH control were changed as −44.09% as compared with intact vehicle control, but they were changed as 30.60, 41.84, 41.96, 65.17, 57.39 and 42.24% in TB 50 mg/kg, AR and KOG 400 mg/kg, SKOG 400, 200 and 100 mg/kg oral administered mice as compared with those of NH$_4$OH control mice, respectively.

Mean thicknesses of trachea wall in NH$_4$OH control were changed as 36.49% as compared with intact vehicle control, but they were changed as −13.23, −15.79, −15.51, −22.15, −20.39 and −15.97% in TB 50 mg/kg, AR and KOG 400 mg/kg, SKOG 400, 200 and 100 mg/kg oral administered mice as compared with those of NH$_4$OH control mice, respectively.

Mean thicknesses of trachea epithelium in NH4OH control were changed as 160.98% as compared with intact vehicle control, but they were changed as −35.48, −38.52, −36.41, −49.59, −47.39 and −36.70% in TB 50 mg/kg, AR and KOG 400 mg/kg, SKOG 400, 200 and 100 mg/kg oral administered mice as compared with those of NH$_4$OH control mice, respectively.

Mean thicknesses of trachea submucosa in NH$_4$OH control were changed as 236.33% as compared with intact vehicle control, but they were changed as −47.27, −49.85, −55.07, −66.23, −63.54 and −52.73% in TB 50 mg/kg, AR and KOG 400 mg/kg, SKOG 400, 200 and 100 mg/kg oral administered mice as compared with those of NH$_4$OH control mice, respectively.

Mean numbers of infiltrated inflammatory cells on the trachea of NH4OH control were changed as 1999.53% as compared with intact vehicle control, but they were changed as −62.74, −63.79, −59.03, −80.97, −73.14 and −60.47% in TB 50 mg/kg, AR and KOG 400 mg/kg, SKOG 400, 200 and 100 mg/kg oral administered mice as compared with those of NH$_4$OH control mice, respectively.

Mean numbers of infiltrated mast cells on the trachea of NH$_4$OH control were changed as 3125.00% as compared with intact vehicle control, but they were changed as −63.05, −77.78, −78.29, −95.35, −90.44 and −77.52% in TB 50 mg/kg, AR and KOG 400 mg/kg, SKOG 400, 200 and 100 mg/kg oral administered mice as compared with those of NH$_4$OH control mice, respectively.

Mean ASA in NH$_4$OH control were changed as −60.77% as compared with intact vehicle control, but they were changed as 65.26, 73.98, 69.16, 130.52, 101.33 and 72.48% in TB 50 mg/kg, AR and KOG 400 mg/kg, SKOG 400, 200 and 100 mg/kg oral administered mice as compared with those of NH$_4$OH control mice, respectively.

Mean thicknesses of alveolar septum in NH$_4$OH control were changed as 889.73% as compared with intact vehicle control, but they were changed as −57.84, −62.41, −61.37, −82.66, −72.02 and −61.34% in TB 50 mg/kg, AR and KOG 400 mg/kg, SKOG 400, 200 and 100 mg/kg oral administered mice as compared with those of NH$_4$OH control mice, respectively.

Mean numbers of infiltrated inflammatory cells on the alveolar septum of NH$_4$OH control were changed as 3034.05% as compared with intact vehicle control, but they were changed as −73.92, −75.95, −73.89, −87.59, −81.58 and −74.46% in TB 50 mg/kg, AR and KOG 400 mg/kg, SKOG 400, 200 and 100 mg/kg oral administered mice as compared with those of NH$_4$OH control mice, respectively.

Example 4. Expectorant Assay (1) Animals and Husbandry

One-hundred twenty one 6-week male SPF/VAF CrljOri: CD1[ICR] mice (OrientBio, Seungnam, Korea; body weight ranged in 29-32 g upon receipt) were prepared, and seven groups of 10 mice each were selected based on the body weights at 7 days after acclimatization based on the body weights (Average:34.75±1.32 g, ranged in 31.6-37.4 g), as follows. Animals husbandries were conducted as same as antitussive assay. All laboratory animals were treated according to the national regulations of the usage and welfare of laboratory animals, and approved by the Institutional Animal Care and Use Committee in Daegu Haany University (Gyeongsan, Gyeongbuk, Korea) [DHU2016-035, Apr. 22, 2016; ANNEX IV].

Experimental groups (Seven groups, 10 mice in each group were finally sacrificed)
1. Control: Vehicle (distilled water) treated intact control mice
2. AM: AM 250 mg/kg administered mice
3. AR: AR 400 mg/kg administered mice
4. KOG: KOG 400 mg/kg administered mice
5. SKOG400: SKOG 400 mg/kg administered mice
6. SKOG200: SKOG 200 mg/kg administered mice
7. SKOG100: SKOG 100 mg/kg administered mice (2) Test Substance Administration AR, KOG and SKOG were orally administered as same as antitussive assay, once a day for 11 days before phenol red treatment. In addition, AM was also dissolved in distilled water as 25 mg/ml concentrations, and orally administered in a volume of 10 ml/kg (as equivalence to 250 mg/kg), once a day for 11 days before phenol red treatment. In intact vehicle control mice, distilled water 10 ml/kg was orally administered, instead of AR, KOG, SKOG or AM to provide same restrain stresses, in the present experiment.

(3) Body Weight Measurements

Changes of body weights and gains were measured as same methods described in Example 3. The results are shown in Table 7 and FIG. 6.

TABLE 7

| Periods | Body weights (g) at test material administration | | Body weight gains (g) |
|---|---|---|---|
| Groups | First [A] | Last [B] | [B − A] |
| Control | | | |
| Intact | 29.09 ± 1.23 | 30.96 ± 1.01 | 1.87 ± 0.60 |
| Reference | | | |
| AM 250 mg/kg | 29.23 ± 1.16 | 31.22 ± 1.65 | 1.99 ± 0.73 |
| AR 400 mg/kg | 29.40 ± 0.81 | 31.11 ± 1.25 | 1.71 ± 0.85 |
| KOG 400 mg/kg | 29.00 ± 1.60 | 30.69 ± 1.77 | 1.69 ± 0.90 |
| SKOG | | | |
| 400 mg/kg | 29.26 ± 1.12 | 31.01 ± 1.76 | 1.75 ± 1.02 |
| 200 mg/kg | 29.20 ± 1.26 | 31.25 ± 1.83 | 2.05 ± 0.92 |
| 100 mg/kg | 29.18 ± 1.04 | 31.23 ± 1.76 | 2.05 ± 1.03 |

Values are expressed mean ± SD of 10 mice.

Figure 6:
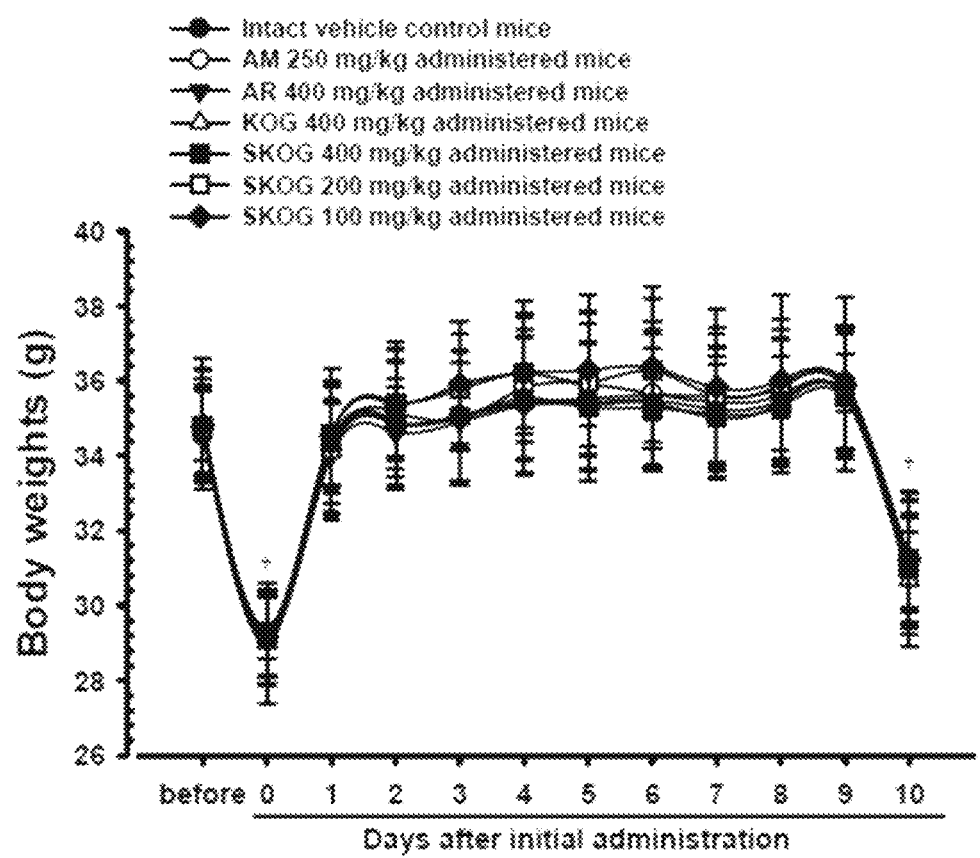
FIG. 6 is a graph showing the body weight change of experimental animals in the expectorant effect measurement by SKOG administration.

FIG. 6 shows the body weight change of experimental animals in the expectorant effect measurement by SKOG administration.

No significant changes on the body weights and gains during 11 days of continuous oral administration periods were detected in AM 250 mg/kg, AR and KOG 400 mg/kg, SKOG 400, 200 and 100 mg/kg treated mice as compared with those of intact vehicle control mice, respectively. In addition, no significant changes on the body weights and gains were demonstrated in SKOG 400, 200 and 100 mg/kg treated mice as compared to those of AR and KOG 400 mg/kg, in our study (Table 7 and FIG. 6).

The body weight gains during 11 days of continuous oral administration periods in AM 250 mg/kg, AR and KOG 400 mg/kg, SKOG 400, 200 and 100 mg/kg oral administered mice were changed as 6.42, −8.56, −9.63, −6.42, 9.63 and 9.63% as compared with intact vehicle control, respectively.

(4) Body Surface Gross Findings

Figure 7:
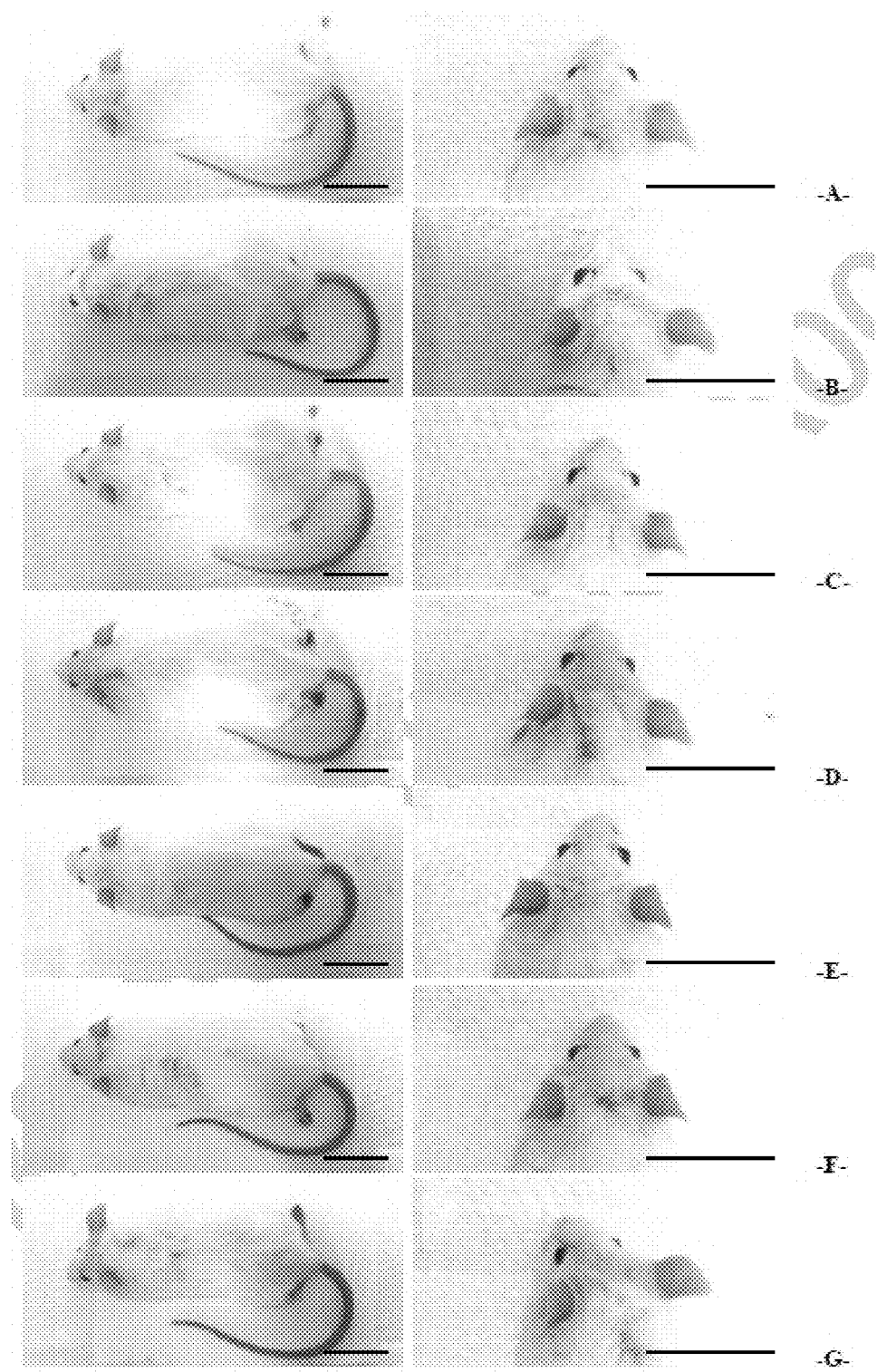
FIG. 7 shows the visual change of body surfaces of experimental animals by SKOG administration. A: normal control group, B: AM 250 mg/kg administered group, C: AR 400 mg/kg administered group, D: KOG 400 mg/kg administered group, E: SKOG 400 mg/kg administered group, F: SKOG 200 mg/kg administered group, G: SKOG 100 mg/kg administered group. Scale bars indicate 120 μm.

FIG. 7 shows the visual change of body surfaces of experimental animals by SKOG administration.

Noticeable and dose-dependent increases of body redness were demonstrated in SKOG 400, 200 and 100 mg/kg as compared with those of intact vehicle control mice, indicating increases of intraperitoneal injected phenol red uptake and secretion, respectively. In addition, AR and KOG 400 mg/kg, AM 250 mg/kg treated mice also showed dramatic increases of body redness at 30 min after intraperitoneal injection of phenol red solutions as compared with those of intact control mice, respectively. Especially, SKOG 400 and 200 mg/kg showed obvious increases of body surface redness gross signs as compared with those of AR and KOG 400 mg/kg, and SKOG 100 mg/kg showed similar body surface redness gross signs as compared with those of AR and KOG 400 mg/kg, respectively. In addition, AR and KOG 400 mg/kg, SKOG 100 mg/kg showed similar or more favorable increases of body surface redness gross signs as compared to those of AM 250 mg/kg, in the current experiment (FIG. 7).

(5) Measurement of Mucous Secretions

Mucous secretions were measured by single intraperitoneal injection of 5% phenol red (Junsei Chemical Co. Ltd., Tokyo, Japan) solution, dissolved in saline (w/v) 10 ml/kg at 30 min after last 11th test substance administration, and 30 min after phenol red solution injection, all mice were sacrificed by cervical dislocation without damaging the trachea, after gross image acquirement to observe body surface redness, individually. After dissected free from adjacent organs, the trachea was removed from the thyroid cartilage to the main stem bronchi. After ultrasonic for 15 min using ultrasonicator (Model 5210, Branson Ultrasonics, Danbury, Conn., USA), 1 ml $NaHCO_3$ solution (5%, w/v) add to the normal saline, and optical density of these prepared trachea lavage fluid (TLF) were measured at 546 nm using a microplate reader (Model Sunrise, Tecan, Männedorf, Switzerland) as described previously with some modifications.

Figure 8:
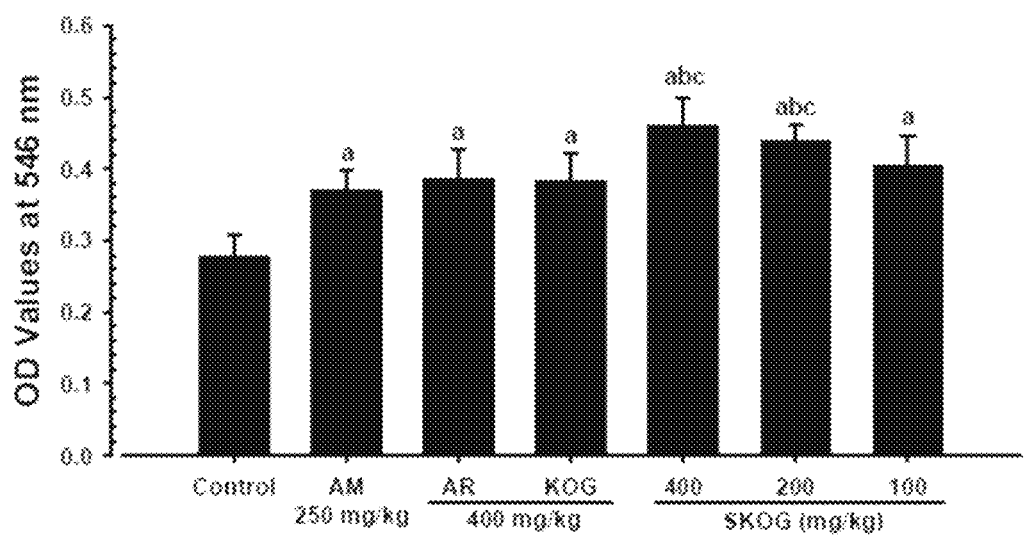
FIG. 8 shows the mucus secretion change of experimental animals by SKOG administration.

FIG. 8 shows the mucus secretion change of experimental animals by SKOG administration.

Significant ($p<0.01$) and dose-dependent increases of the TLF OD values were demonstrated in SKOG 400, 200 and 100 mg/kg as compared with those of intact vehicle control mice at 30 min after intraperitoneal injection of phenol red solutions, indicating increases of the trachea mucous secretion, respectively. In addition, AR and KOG 400 mg/kg, AM 250 mg/kg treated mice also showed significant ($p<0.01$) increases of the TLF OD values as compared with those of intact vehicle control mice, respectively. Especially, SKOG 400 and 200 mg/kg showed significantly ($p<0.01$) increased TLF OD values as compared with those of AR and KOG 400 mg/kg, and SKOG 100 mg/kg showed similar favorable mucous secretion increase effects as compared with those of AR and KOG 400 mg/kg, respectively. In addition, AR and KOG 400 mg/kg, SKOG 100 mg/kg showed similar or more favorable TLF OD values as compared to those of AM 250 mg/kg, in the present experiment (FIG. 8).

The TLF OD values in AM 250 mg/kg, AR and KOG 400 mg/kg, SKOG 400, 200 and 100 mg/kg oral administered mice were changed as 33.95, 40.17, 39.29, 66.96, 58.78 and 46.27% as compared with intact vehicle control, respectively.

(6) Histopathology

Simultaneously, some parts of individual lung (left lateral lobes) were sampled at trachea excisions, and fixed in 10% NBF, and crossly trimmed. Then embedded in paraffin, sectioned (3~4 μm) and stained with H&E for general histopathology or PAS (periodic acid schiff) for mucous producing cells, and after that the histopathological profiles of each sample were observed under light microscope. To more detail changes, mean thicknesses of secondary bronchus mucosa, numbers of PAS positive mucous producing cells on the secondary bronchus (cells/$mm^2$) were analyzed using a computer-assisted image analysis program, according to previously established methods, respectively. The histopathologist was blinds to group distribution when this analysis was made, and at least five repeated measurements in same histological specimens prepared were considered to calculate each mean histomorphometrical value, whenever possible, in this histopathological evaluation.

Figure 9:
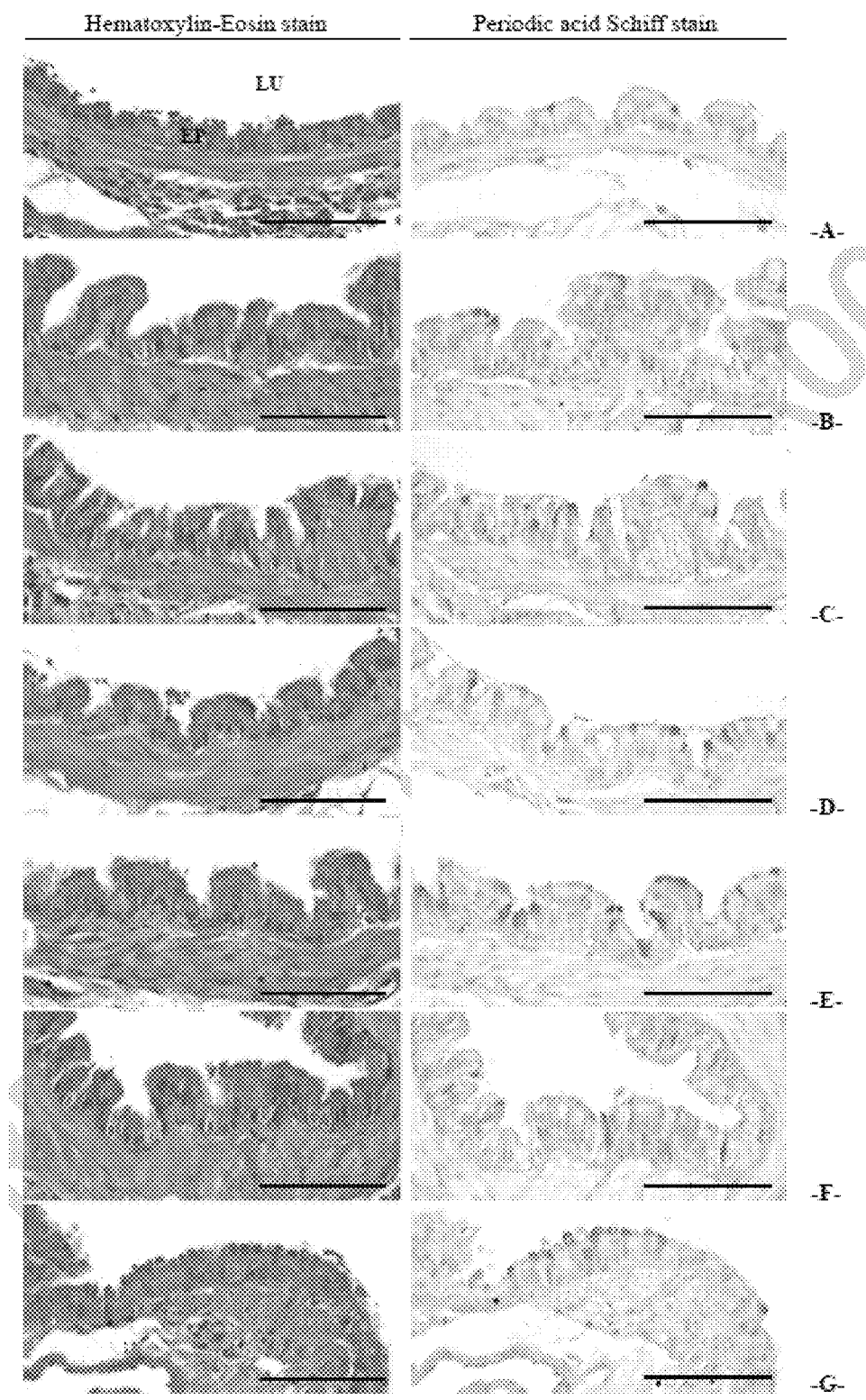
FIG. 9 shows the histopathological change of intrapulmonary secondary bronchus mucosa of experimental animals by SKOG administration. "LU" and "EP" represent lumen and epithelium, respectively. A: normal control group, B: AM 250 mg/kg control group, C: AR 400 mg/kg administered group, D: KOG 400 mg/kg administered group, E: SKOG 400 mg/kg administered group, F: SKOG 200 mg/kg administered group, G: SKOG 100 mg/kg administered group. Scale bars indicate 60 μm.

FIG. 9 shows the histopathological change of intrapulmonary secondary bronchus mucosa of experimental animals by SKOG administration.

Figure 10:
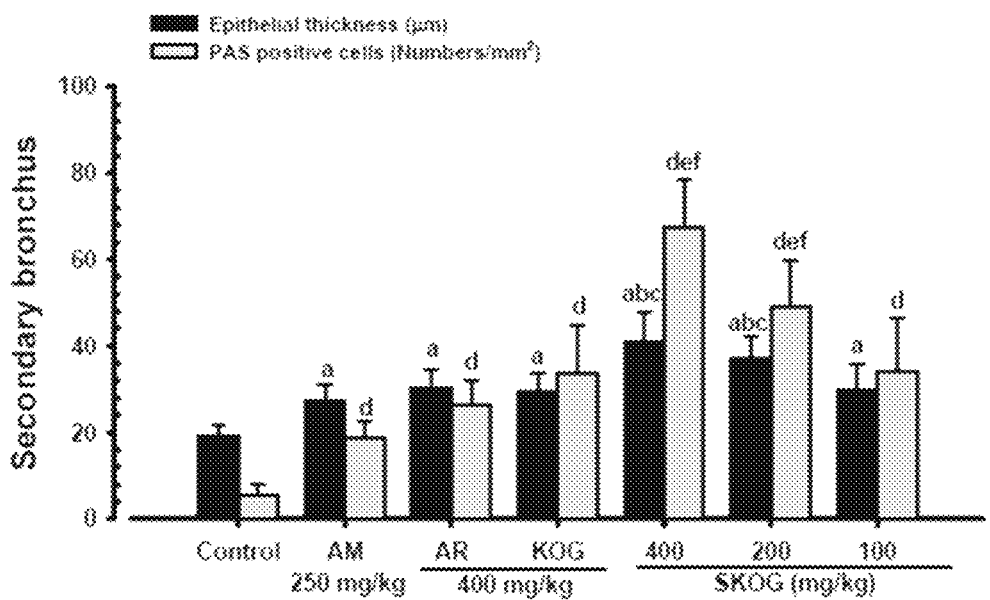
FIG. 10 shows the thickness change of intrapulmonary secondary bronchus mucosa and the numerical increase change of PAS positive cells in experimental animals by SKOG administration.

FIG. 10 shows the thickness change of intrapulmonary secondary bronchus mucosa and the numerical increase change of PAS positive cells in experimental animals by SKOG administration.

Significant ($p<0.01$ or $p<0.05$) and dose-dependent increases of the intrapulmonary secondary bronchus mucosa thicknesses and PAS positive mucous producing cells were observed in SKOG 400, 200 and 100 mg/kg treated mice as compared to those of intact vehicle control mice, suggesting increases of mucous secretion or activity of bronchus mucosa, respectively. In addition, AR and KOG 400 mg/kg, AM 250 mg/kg also significantly ($p<0.01$) increased the intrapulmonary secondary bronchus mucosa thicknesses and PAS positive mucous producing cell numbers as compared with those of intact vehicle control mice, respectively. Especially, SKOG 400 and 200 mg/kg showed significantly ($p<0.01$) increased intrapulmonary secondary bronchus mucosa thicknesses and PAS positive mucous producing cell numbers as compared with those of AR and KOG 400 mg/kg, and SKOG100 mg/kg showed similar the intrapulmonary secondary bronchus mucosa thicknesses and PAS positive mucous producing cell numbers as compared with those of AR and KOG 400 mg/kg, respectively. In addition, AR and KOG 400 mg/kg, SKOG 100 mg/kg showed similar or more favorably increased the intrapulmonary secondary bronchus mucosa thicknesses and PAS positive mucous producing cell numbers as compared to those of AM 250 mg/kg, in this experiment (FIGS. 9 and 10).

Mean thicknesses of secondary bronchus mucosa in AM 250 mg/kg, AR and KOG 400 mg/kg, SKOG 400, 200 and 100 mg/kg oral administered mice were changed as 41.69, 56.73, 51.59, 111.08, 91.95 and 54.99% as compared with intact vehicle control, respectively.

Mean numbers of secondary bronchus epithelial PAS positive mucous producing cells in AM 250 mg/kg, AR and KOG 400 mg/kg, SKOG 400, 200 and 100 mg/kg oral administered mice were changed as 231.58, 364.91, 492.98, 1082.46, 761.40 and 498.25% as compared with intact vehicle control, respectively

Example 5. Anti-Inflammatory Assay (1) Animals and Husbandry

One-hundred thirty two 6-week male SPF/VAF CrljOri: CD1 [ICR] mice (OrientBio, Seungnam, Korea; body weight ranged in 29-32 g upon receipt) were prepared, and eight groups of 10 mice each were selected based on the body weights at 7 days after acclimatization based on the body weights (intact control: 33.88±1.11 g, ranged in 31.8~35.4 g; Xylene treated mice: 33.85±1.32 g, ranged in 31.1-36.6 g), as follows. Animals husbandries were conducted as same as antitussive and expectorant assays. All laboratory animals were treated according to the national regulations of the usage and welfare of laboratory animals, and approved by the Institutional Animal Care and Use Committee in Daegu Haany University (Gyeongsan, Gyeongbuk, Korea) [DHU2016-036, Apr. 22, 2016; ANNEX V].

Experimental groups (Eight groups, 10 mice in each group were finally sacrificed)

1. Intact vehicle control: Vehicle (distilled water) treated intact control mice 2. Xylene control: Vehicle administered and xylene topically applied control mice 3. DEXA: DEXA 1 mg/kg administered and xylene topically applied mice 4. AR: AR 400 mg/kg administered and xylene topically applied mice 5. KOG: KOG 400 mg/kg administered and xylene topically applied mice 6. SKOG400: SKOG 400 mg/kg administered and xylene topically applied mice 7. SKOG200: SKOG 200 mg/kg administered and xylene topically applied mice 8. SKOG100: SKOG 100 mg/kg administered and xylene topically applied mice (2) Test Substance Administration AR, KOG and SKOG were orally administered as same as antitussive and expectorant assays, once a day for 11 days before xylene topical applications. In addition, DEXA-water soluble granules were dissolved indistilled water as 1.5 mg/ml concentrations (0.1 mg/ml based on DEXA itself), and also orally administered in a volume of 10 ml/kg (as equivalence to 1 mg/kg based on DEXA itself), once a day for 11 days before xylene topical applications. In intact vehicle and xylene control mice, distilled water 10 ml/kg was orally administered, instead of AR, KOG, SKOG or DEXA to provide same restrain stresses, in the present experiment.

(3) Body Weight Measurements

Changes of body weights and gains were measured as same methods described in Example 3 and 4.

Figure 11:
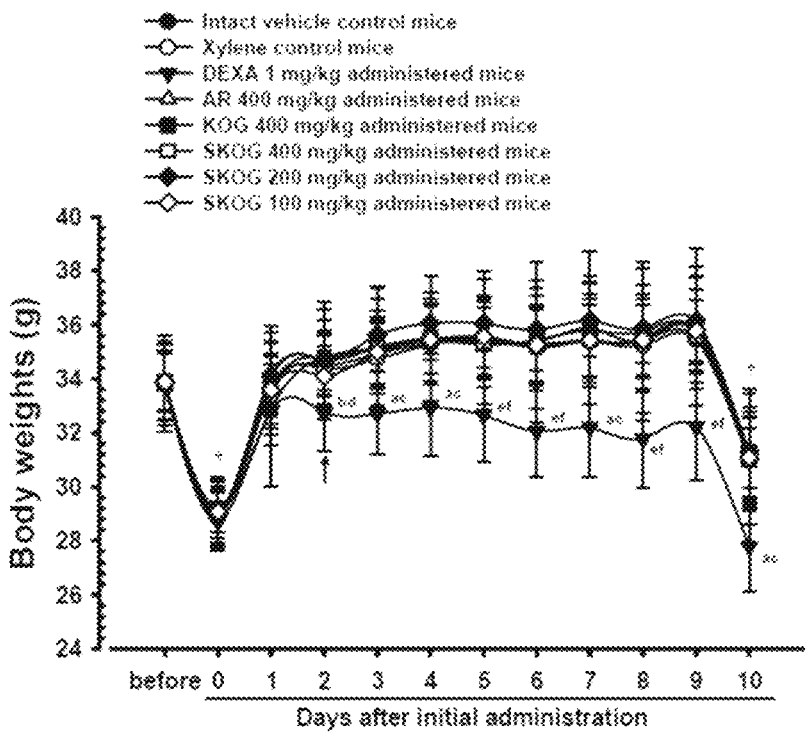
FIG. 11 shows the body weight change of experimental animals in the anti-inflammatory effect measurement by SKOG administration.

The results are shown in Table 8 and FIG. 11.

TABLE 8

| Periods Groups | Body weights (g) at test material administration | | Body weight gains (g) |
|---|---|---|---|
| | First [A] | Last [B] | [B − A] |
| Controls | | | |
| Intact | 28.94 ± 1.06 | 31.04 ± 1.49 | 2.10 ± 0.90 |
| Xylene | 28.93 ± 1.01 | 30.97 ± 1.62 | 2.04 ± 0.79 |
| Reference | | | |
| DEXA 1 mg/kg | 28.72 ± 1.10 | 27.80 ± 1.66$^{ab}$ | −0.92 ± 0.76$^{ab}$ |
| AR 400 mg/kg | 28.99 ± 1.21 | 31.12 ± 2.51 | 2.13 ± 1.63 |
| KOG 400 mg/kg | 29.20 ± 1.11 | 31.02 ± 1.78 | 1.82 ± 1.01 |
| SKOG | | | |
| 400 mg/kg | 29.11 ± 1.27 | 31.29 ± 2.19 | 2.18 ± 1.34 |
| 200 mg/kg | 28.95 ± 1.26 | 31.29 ± 1.66 | 2.34 ± 0.70 |
| 100 mg/kg | 29.07 ± 0.72 | 31.08 ± 1.10 | 2.01 ± 0.86 |

Values are expressed mean ± SD of 10 mice.

FIG. 11 shows the body weight change of experimental animals in the anti-inflammatory effect measurement by SKOG administration.

No significant changes on the body weights and gains during 11 days of continuous oral administration periods were detected in xylene control mice as compared with those of intact vehicle control mice, respectively. In addition, no significant changes on the body weights and gains were demonstrated in all three different dosages of SKOG 400, 200 and 100 mg/kg, AR and KOG 400 mg/kg treated mice as compared with those of xylene control mice, and no significant changes on the body weights and gains were also demonstrated in SKOG 400, 200 and 100 mg/kg treated mice as compared to those of AR and KOG 400 mg/kg, respectively. But DEXA 1 mg/kg treated mice showed significant ($p<0.01$ or $p<0.05$) decreases of body weights from 2 days after initial administration as compared with those of intact vehicle and xylene control mice, and also significant ($p<0.01$) decreases in body weight gains during 11 days of continuous oral administration periods as compared with those of intact vehicle and xylene control mice, in our experiment (Table 8, FIG. 11).

The body weight gains during 11 days of continuous oral administration periods in xylene control were changed as −2.86% as compared with intact vehicle control, and they were changed as −145.10, 4.41, −10.78, 6.86, 14.71 and −1.47% in DEXA 1 mg/kg, AR and KOG 400 mg/kg, SKOG 400, 200 and 100 mg/kg oral administered mice as compared with those of xylene control mice, respectively.

(4) Acute Inflammation Inducement

Acute inflammations were induced by single topical application of 0.03 ml of xylene (Duksan Pure Chemical Co. Ltd., Ansan, Korea) to the anterior surface of the right ear at 1 hour after last 11th test substance administration, as described previously with some modifications. Equal volume of saline was topically applied in intact vehicle mouse ears, instead of xylene, in our experiment.

(5) Ear Weight Measurement

Two hours after topical application of xylene, circular sections of induced ear were taken using a cork borer with a 7-mm diameter and weighed as absolute wet-weights, and then the relative weights (% of bodyweights) of the ears were calculated to reduce the differences from individual body weights, as follow Equation [2], in the current experiment.

Relative ear weights(% vs body weights)=(Absolute ear wet-weights/body weight at sacrifice)×100   EQUATION [2]

Figure 12:
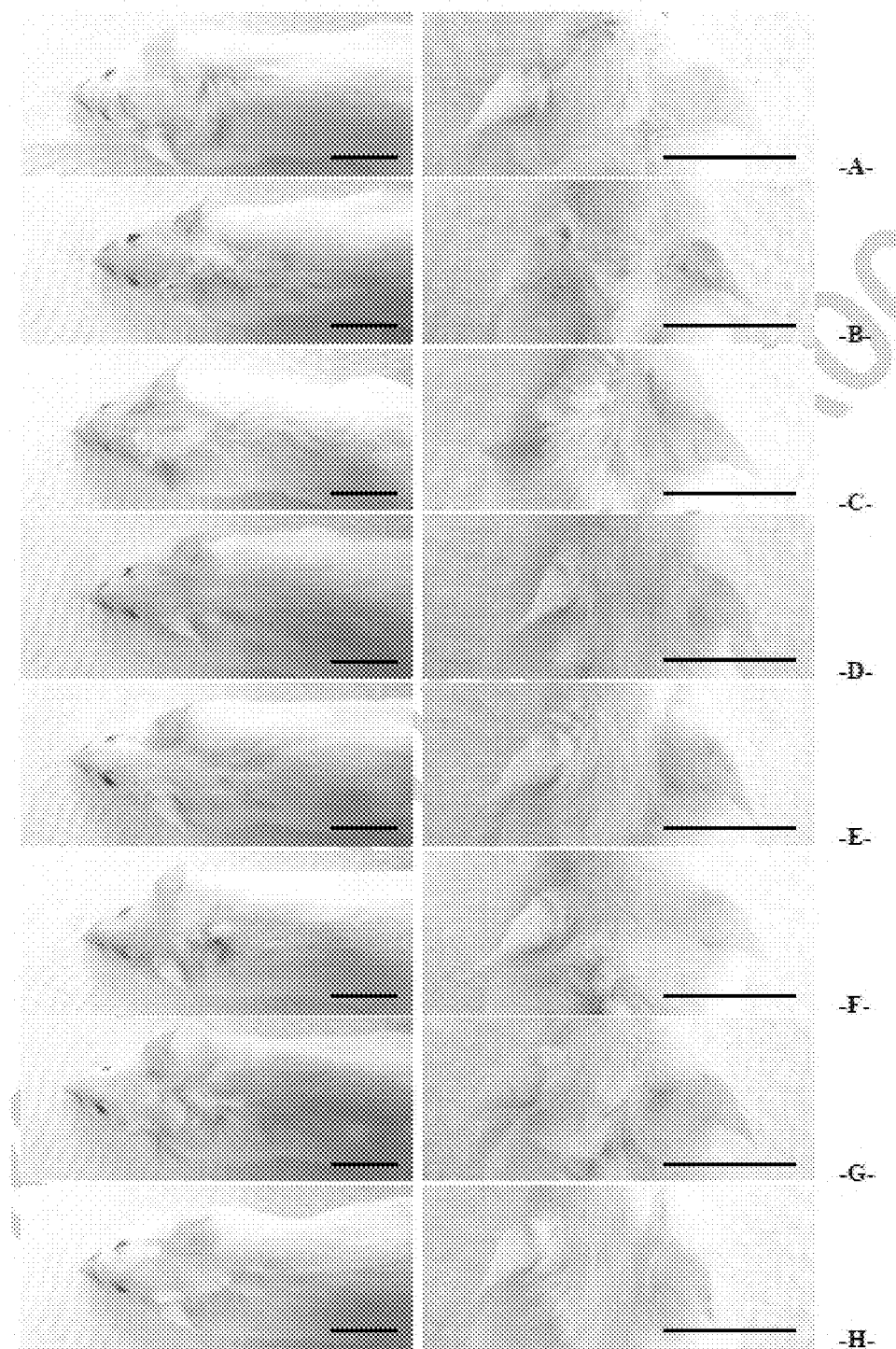
FIG. 12 shows the visual change of ears of experimental animals by SKOG administration. A: normal control group, B: xylene control group, C: dexamethasone 1 mg/kg administered group, D: AR 400 mg/kg administered group, E: KOG 400 mg/kg administered group, F: SKOG 400 mg/kg administered group, G: SKOG 200 mg/kg administered group, H: SKOG 100 mg/kg administered group. Scale bars indicate 16 μm.

FIG. 12 shows the visual change of ears of experimental animals by SKOG administration.

Noticeable acute inflammatory response related ear redness and edema were observed in xylene control mice at 2 hours after xylene topical applications as compared with intact vehicle control mice. However, these gross xylene-induced redness and edema findings were dose-dependently and dramatically inhibited by 11 days of continuous oral pre-administration of SKOG 400, 200 and 100 mg/kg as compared with those of xylene control mice, respectively. In addition, AR and KOG 400 mg/kg, DEXA 1 mg/kg treated mice also showed obvious decreases of the ear redness and edema as compared with those of xylene control mice at gross inspections, respectively. Especially, SKOG 400 and 200 mg/kg showed clear decreases of ear redness and edema gross signs as compared with those of AR and KOG 400 mg/kg, and SKOG 100 mg/kg showed similar xylene-induced ear redness and edema gross signs as compared with those of AR and KOG 400 mg/kg, respectively. In addition, SKOG 400 mg/kg showed favorable decreases of ear redness and edema gross signs as comparable to those of DEXA 1 mg/kg, but AR and KOG 400 mg/kg, SKOG 200 and 100 mg/kg showed slighter inhibitory effects on the xylene-induced ear redness and edema as compared to those of DEXA 1 mg/kg, in the current gross observation (FIG. 12).

Figure 13:
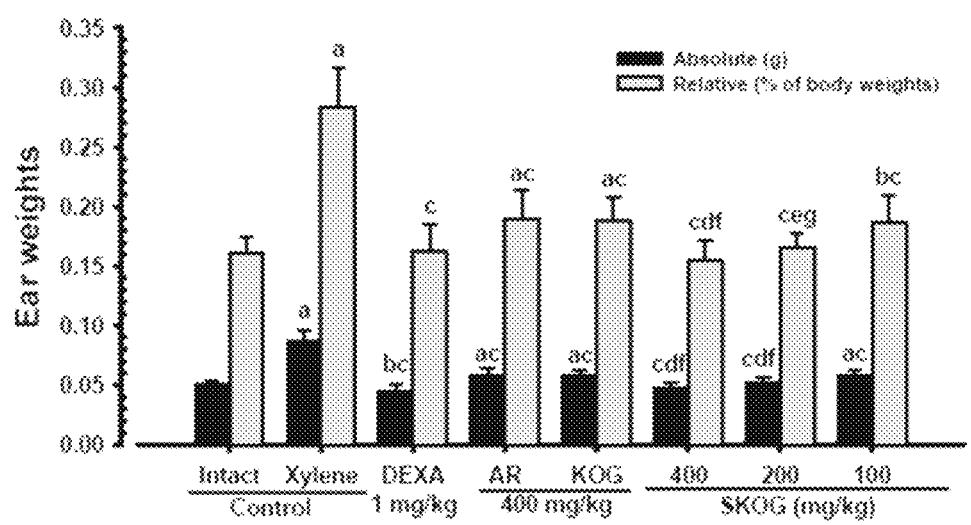
FIG. 13 shows the ear weight change of experimental animals by SKOG administration.

FIG. 13 shows the ear weight change of experimental animals by SKOG administration.

Significant ($p<0.01$) increases of the ear absolute and relative weights were demonstrated in xylene control mice as compared with intact vehicle control mice at 2 hours after xylene topical applications. However, significant ($p<0.01$) and dose-dependent decreases of the ear absolute and relative weights were observed in SKOG 400, 200 and 100 mg/kg as compared with those of xylene control mice, respectively. In addition, AR and KOG 400 mg/kg, DEXA 1 mg/kg treated mice also showed significant ($p<0.01$) decreases of the ear absolute and relative weights as compared with those of xylene control mice, respectively. Especially, SKOG400 and 200 mg/kg showed significant ($p<0.01$ or $p<0.05$) decreases of ear weights as compared with those of AR and KOG 400 mg/kg, and SKOG 100 mg/kg showed similar inhibitory activities against xylene induced ear weight increases as compared with those of AR and KOG 400 mg/kg, respectively. In addition, SKOG 400 mg/kg showed favorable inhibitory effects on the absolute and relative ear weight increased induced by topical application of xylene as comparable to those of DEXA 1 mg/kg, but AR and KOG 400 mg/kg, SKOG 200 and 100 mg/kg showed slighter inhibitory effects on the xylene-induced ear weight increases as compared to those of DEXA 1 mg/kg, in the present observation (FIG. 13).

The absolute ear weights in xylene control were changed as 75.20% as compared with intact vehicle control, but they were changed as −48.52, −32.99, −33.45, −45.09, −40.87 and −34.25% in DEXA 1 mg/kg, AR and KOG 400 mg/kg, SKOG 400, 200 and 100 mg/kg oral administered mice as compared with those of xylene control mice, respectively.

The relative ear weights in xylene control were changed as 76.00% as compared with intact vehicle control, but they were changed as −42.61, −33.18, −33.55, −45.62, −41.67 and −34.47% in DEXA 1 mg/kg, AR and KOG 400 mg/kg, SKOG 400, 200 and 100 mg/kg oral administered mice as compared with those of xylene control mice, respectively.

(6) Histopathology

After ear weight measurement, individual ear samples were fixed in 10% NBF, and crossly trimmed. Then embedded in paraffin, sectioned (3~4 μm) and stained with Hematoxylin and eosin (H&E) for general histopathology or toluidine blue for mast cells, and after that the histopathological profiles of each sample were observed under light microscope. To more detail changes, mean total, epidermis and dermis thicknesses of the ear anterior surface, numbers of infiltrated inflammatory cells and mast cells on the dermis of ear (cells/mm$^2$), collagen occupied region percentages on the dermis (%/mm2) were analyzed using a computer assisted image analysis program, according to previously established methods, respectively. The histopathologist was blinds to group distribution when this analysis was made, and at least five repeated measurements in same histological specimens prepared were considered to calculate each mean histomorphometrical value, whenever possible, in this histopathological evaluation.

Figure 14:
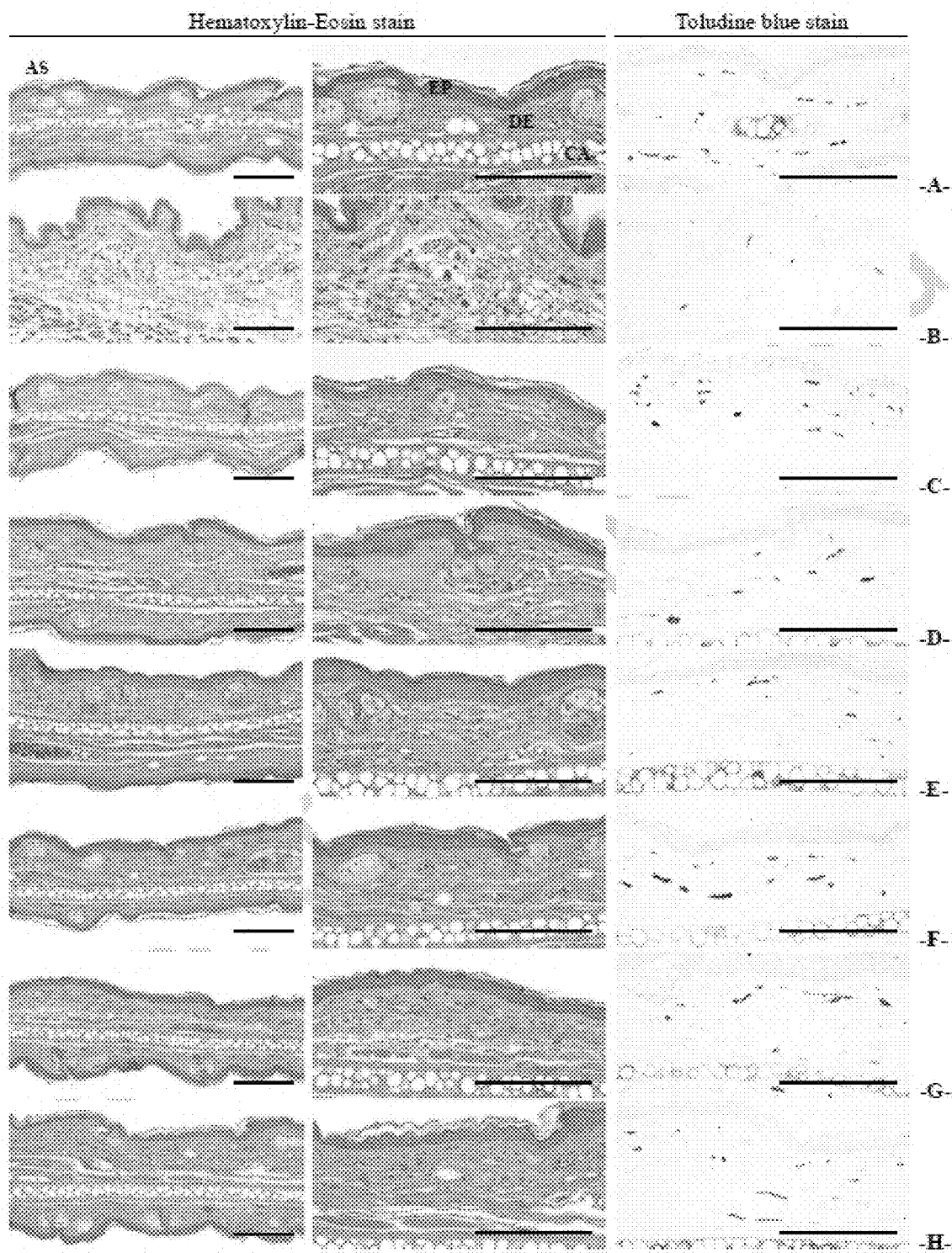
FIG. 14 shows the histopathological change of ear skin tissues of experimental animals by SKOG administration. "AS", "EP", "DE", and "CA" represent anterior surface, epidermis, dermis, and cartilage, respectively. A: normal control group, B: xylene control group, C: dexamethasone 1 mg/kg administered group, D: AR 400 mg/kg administered group, E: KOG 400 mg/kg administered group, F: SKOG 400 mg/kg administered group, G: SKOG 200 mg/kg administered group, H: SKOG 100 mg/kg administered group. Scale bars indicate 120 μm.

The results are shown in Table 9 and FIG. 14.

TABLE 9

| | Index | | | | | |
|---|---|---|---|---|---|---|
| | Thickness (μm) | | | Cells (Numbers/mm$^2$) | | Collagen fiber |
| Groups | Total | Epidermis | Dermis | Inflammatory | Mast | (%/mm$^2$ of dermis) |
| Controls | | | | | | |
| Intact | 103.41 ± 11.47 | 8.98 ± 0.93 | 54.86 ± 11.97 | 15.20 ± 4.66 | 69.00 ± 15.48 | 78.31 ± 9.75 |
| Xylene | 264.48 ± 30.02$^f$ | 9.07 ± 1.16 | 132.28 ± 22.16$^f$ | 263.40 ± 55.50$^f$ | 8.20 ± 4.16$^a$ | 26.74 ± 6.58$^f$ |
| Reference | | | | | | |
| TB 50 mg/kg | 99.55 ± 9.57$^h$ | 8.50 ± 1.65 | 52.33 ± 13.72$^h$ | 10.10 ± 10.54$^{fh}$ | 61.30 ± 12.65$^c$ | 77.43 ± 12.79$^h$ |
| AR 400 mg/kg | 166.51 ± 17.59$^{fh}$ | 8.77 ± 0.71 | 75.41 ± 8.63$^{fh}$ | 72.30 ± 14.17$^{fh}$ | 45.20 ± 10.52$^{ac}$ | 64.73 ± 10.85$^{gh}$ |
| KOG 400 mg/kg | 158.83 ± 13.35$^{fh}$ | 8.76 ± 0.82 | 71.55 ± 5.05$^{fh}$ | 69.00 ± 12.00$^{fh}$ | 42.40 ± 6.72$^{ac}$ | 67.59 ± 4.70$^{gh}$ |
| SKOG | | | | | | |
| 400 mg/kg | 105.94 ± 13.74$^{hij}$ | 9.15 ± 1.09 | 51.58 ± 6.97$^{hij}$ | 29.20 ± 8.26$^{fhij}$ | 61.00 ± 10.92$^{cde}$ | 81.51 ± 7.58$^{hij}$ |
| 200 mg/kg | 128.25 ± 15.08$^{fhij}$ | 8.28 ± 1.18 | 61.37 ± .03$^{hij}$ | 48.40 ± 14.21$^{fhij}$ | 58.20 ± 8.53$^{bcde}$ | 76.84 ± 5.22$^{hij}$ |
| 100 mg/kg | 160.57 ± 18.68$^{fh}$ | 8.73 ± 0.92 | 71.69 ± 10.31$^{fh}$ | 77.70 ± 21.78$^{fh}$ | 42.80 ± 10.09$^{ac}$ | 66.43 ± 10.37$^{gh}$ |

Values are expressed mean ± SD of 10 mice

FIG. 14 shows the histopathological change of ear skin tissues of experimental animals by SKOG administration.

Significant ($p<0.01$) increases ear total and dermis thicknesses, the numbers of infiltrated inflammatory cells on the ear dermis, degranulation related decreases of mast cell numbers in the dermis, decreases of dermis collagen fiber occupied regions, without significant changes on the ear epidermis were observed in xylene control as classic contact acute inflammations—dermatitis related histopathological findings. However, these xylene-induced ear acute contact dermatitis related findings at histopathological inspections were significantly (p<0.01) and dose-dependently inhibited by 11 days of continuous oral pretreatment of SKOG 400, 200 and 100 mg/kg as compared with those of xylene control mice, respectively. In addition, AR and KOG 400 mg/kg, DEXA 1 mg/kg also significantly (p<0.01) reduced the xylene-induced ear acute contact dermatitis related histopathological findings as compared with those of xylene control mice, respectively. Especially, SKOG 400 and 200 mg/kg showed significantly (p<0.01) increased inhibitory effects on the xylene-induced ear acute contact dermatitis related histopathological findings as compared with those of AR and KOG 400 mg/kg, and SKOG 100 mg/kg showed similar inhibitory activities against xylene-induced ear acute contact dermatitis related histopathological findings as compared with those of AR and KOG 400 mg/kg, respectively. In addition, SKOG 400 mg/kg showed favorable inhibitory effects on the xylene-induced ear acute contact dermatitis related histopathological findings as comparable to those of DEXA 1 mg/kg, but AR and KOG 400 mg/kg, SKOG 200 and 100 mg/kg showed slighter inhibitory effects on the xylene-induced ear acute contact dermatitis related histopathological findings as compared to those of DEXA 1 mg/kg, in this observation (Table 9 and FIG. 14).

Mean total ear thicknesses in xylene control were changed as 155.76% as compared with intact vehicle control, but they were changed as −62.39, −37.01, −39.95, −59.94, −51.51 and −39.29% in DEXA 1 mg/kg, AR and KOG 400 mg/kg, SKOG 400, 200 and 100 mg/kg oral administered mice as compared with those of xylene control mice, respectively.

Mean ear epidermis thicknesses in xylene control were changed as 1.02% as compared with intact vehicle control, but they were changed as −6.35, −3.30, −3.45, 0.87, −8.69 and −3.80% in DEXA 1 mg/kg, AR and KOG 400 mg/kg, SKOG 400, 200 and 100 mg/kg oral administered mice as compared with those of xylene control mice, respectively.

Mean ear dermis thicknesses in xylene control were changed as 141.11% as compared with intact vehicle control, but they were changed as −60.02, −42.99, −45.91, −61.01, −53.61 and −45.80% in DEXA 1 mg/kg, AR and KOG 400 mg/kg, SKOG 400, 200 and 100 mg/kg oral administered mice as compared with those of xylene control mice, respectively.

Mean numbers of infiltrated inflammatory cells on the ear dermis in xylene control were changed as 1632.89% as compared with intact vehicle control, but they were changed as −93.13, −72.55, −73.80, −88.91, −81.62 and −70.50% in DEXA 1 mg/kg, AR and KOG 400 mg/kg, SKOG 400, 200 and 100 mg/kg oral administered mice as compared with those of xylene control mice, respectively.

Mean numbers of infiltrated mast cells on the ear dermis in xylene control were changed as −88.12% as compared with intact vehicle control, but they were changed as 647.56, 451.22, 417.07, 643.90, 609.76 and 421.95% in DEXA 1 mg/kg, AR and KOG 400 mg/kg, SKOG 400, 200 and 100 mg/kg oral administered mice as compared with those of xylene control mice, respectively.

Mean percentages of collagen occupied regions on the ear dermis in xylene control were changed as −65.86% as compared with intact vehicle control, but they were changed as 189.63, 142.11, 152.82, 204.88, 187.39 and 148.48% in DEXA 1 mg/kg, AR and KOG 400 mg/kg, SKOG 400, 200 and 100 mg/kg oral administered mice as compared with those of xylene control mice, respectively.

What is claimed is:

1. A method for alleviating or treating an inflammatory disease, the method comprising administering, to a subject, a composition comprising *Panax ginseng, Adenophora triphylla, Wolfiporia extensa, Rehmannia glutinosa*, and mel,
    wherein the inflammatory disease is selected from the group consisting of dermatitis, edema, atopic disease, conjunctivitis, periodontitis, rhinitis, otitis media, laryngopharingitis, tonsillitis, stomach ulcer, gastritis, Crohn's disease, colitis, hemorrhoids, gout, ankylosing spondylitis, rheumatic fever, lupus, fibromyalgia, psoriatic arthritis, osteoarthritis, rheumatoid arthritis, periarthritis, tendinitis, tendovaqinitis, peritendinitis, myositis, hepatitis, cystitis, nephritis, Sjogren's syndrome and multiple sclerosis.

2. The method of claim 1, wherein the composition comprises 4-5 wt % of *Panax ginseng,* 4-5 wt % of *Adenophora triphylla,* 8-10 wt % of *Wolfiporia extensa,* 43-48 wt % of *Rehmannia glutinosa,* and 35-40 wt % of mel.

* * * * *